United States Patent

Janssens et al.

[11] Patent Number: 6,110,939
[45] Date of Patent: Aug. 29, 2000

[54] (BENZIMIDAZOLYL- AND IMIDAZOPYRIDINYL) CONTAINING 1-(1,2-DISUBSTITUTED PIPERIDINYL) DERIVATIVES

[75] Inventors: Frans Eduard Janssens, Bonheiden; François Maria Sommen, Wortel; Dominique Louis Nester Ghislaine Surleraux, Machelen; Joseph Elisabeth Leenaerts, Rijkevorsel, all of Belgium

[73] Assignee: Janssen Pharmaceutica N.V., Beerse, Belgium

[21] Appl. No.: 09/102,121

[22] Filed: Jun. 19, 1998

Related U.S. Application Data

[63] Continuation of application No. PCT/EP96/05877, Dec. 20, 1996.

[30] Foreign Application Priority Data

Dec. 27, 1995 [EP] European Pat. Off. ............ 95 203 653
Dec. 27, 1995 [EP] European Pat. Off. ............ 95 203 650

[51] Int. Cl.[7] ................. A61K 31/4418; A61K 31/4439; A61K 31/444; C07D 401/12; C07D 401/14
[52] U.S. Cl. .......................... 514/322; 546/199; 546/187; 546/168; 546/118; 540/603; 544/364; 544/355
[58] Field of Search ............................. 546/199; 514/322

[56] References Cited

U.S. PATENT DOCUMENTS 5,814,636 9/1998 Katano et al. ...................... 514/252

FOREIGN PATENT DOCUMENTS

| 0 151 826 A1 | 8/1985 | European Pat. Off. . |
| 0 232 937 A2 | 8/1987 | European Pat. Off. . |
| 0 282 133 A2 | 9/1988 | European Pat. Off. . |
| WO 96/10562 | 4/1996 | WIPO . |
| WO 97/16440 | 5/1997 | WIPO . |

*Primary Examiner*—Laura L. Stockton
*Attorney, Agent, or Firm*—Mary Appollina

[57] ABSTRACT

This invention concerns the compounds of formula

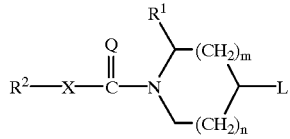

(I)

the N-oxide forms, the pharmaceutically acceptable addition salts and the stereochemically isomeric forms thereof, wherein n is 0, 1 or 2; m is 1 or 2, provided that if m is 2, then n is 1; X is a covalent bond or a bivalent radical of formula —O—, —S—, —NR$^3$—; =Q is =O or =NR$^3$; R$^1$ is Ar$^1$, Ar$^1$C$_{1-6}$alkyl or di(Ar$^1$)C$_{1-6}$alkyl wherein the C$_{1-6}$alkyl group is optionally substituted; R$^2$ is Ar$^2$, Ar$^2$C$_{1-6}$alkyl, Het or HetC$_{1-6}$alkyl; L is a benzimidazole or imidazopyridine derivative of formula (A) or (B) Ar$^1$ is optionally substituted phenyl Ar$^2$ is naphtalenyl or optionally substituted phenyl; and Het is an optionally substituted monocyclic or bicyclic heterocycle; as substance P antagonists; their preparation, compositions containing them and their use as a medicine.

15 Claims, No Drawings

(BENZIMIDAZOLYL- AND IMIDAZOPYRIDINYL) CONTAINING 1-(1,2-DISUBSTITUTED PIPERIDINYL) DERIVATIVES

CROSS REFERENCE TO RELATED APPLICATIONS

This application is a continuation of National Stage application under 35 U.S.C. 371 of PCT/EP96/05877 filed Dec. 20, 1996, which claims priority from EP95.203.653.1, filed Dec. 27, 1995, and EP95.203.650.7, filed Dec. 27, 1995.

This invention concerns (benzimidazolyl- and imidazopyridinyl) containing 1-(1,2-disubstituted piperidinyl) derivatives having tachykinin antagonistic activity, in particular substance P antagonistic activity, and their preparation; it further relates to compositions comprising them, as well as their use as a medicine.

Substance P is a naturally occurring neuropeptide of the tachykinin family. There are ample studies showing that substance P and other tachykinins are involved in a variety of biological actions, and therefore, play an essential role in various disorders (Regoli et al., Pharmacological Reviews 46(4), 1994, p. 551–599, "Receptors and Antagonists for Substance P and Related Peptides"). The development of tachykinin antagonists has led to date to a series of peptide compounds of which might be anticipated that they are metabolically too labile to be employed as pharmaceutically active substances (Longmore J. et al., DN&P 8(1), February 1995, p. 5–23, "Neurokinin Receptors"). The present invention concerns nonpeptide tachykinin antagonists, in particular nonpeptide substances antagonists, which in general are metabolically more stable, and hence, may be more appropriate as pharmaceutically active substances.

Several nonpeptide tachykinin antagonists are disclosed in the art. For instance, EP-0,532,456-A, published on Mar. 17, 1993, discloses 1-acylpiperidine compounds, in particular 2-arylalkyl- 1-arylcarbonyl-4-piperidinamine derivatives, and their use as substance P antagonists.

EP-0,151,824-A and EP-0,151,826-A disclose structurally related N-(benzimidazolyl- and imidazopyridinyl)-1-(1-(carbonyl or imino)-4-piperidinyl)-4-piperidinamine, derivatives as histamine- and serotonine antagonists. Also 1-carbonyl-4-(benzimidazolyl- and imidazopyridinyl) piperidine derivatives all having anti-histaminic and anti-allergic activity are disclosed in EP-A-232,937, EP-A-282,133, EP-A-297,661, EP-A-539,421, EP-A-539,420, WO 92/06086 and WO 93/14083.

The present compounds differ from the art compounds by their structure and by their favourable pharmacological properties.

Hence, the present invention concerns novel compounds of formula (I)

the N-oxide forms, the pharmaceutically acceptable addition salts and the stereochemically isomeric forms thereof, wherein n is 0, 1 or 2;
m is 1 or 2, provided that if m is 2, then n is 1;
X is a covalent bond or a bivalent radical of formula —O—, —S—, —$NR^3$—;
=Q is =O or =$NR^3$;
$R^1$ is $Ar^1$, $Ar^1C_{1-6}$alkyl or di($Ar^1$)$C_{1-6}$alkyl wherein the $C_{1-6}$alkyl group is optionally substituted with hydroxy, $C_{1-4}$alkyloxy, oxo or a ketalized oxo substituent of formula —O—$CH_2$—$CH_2$—O— or —O—$CH_2$—$CH_2$—$CH_2$—O—;
$R^2$ is $Ar^2$, $Ar^2C_{1-6}$alkyl, Het or Het$C_{1-6}$alkyl;
L is a radical of formula (A)

(B)

wherein p is 0, 1 or 2;
.....Y— is a bivalent radical of formula —$CH_2$—, —CH(OH)—, —C(=O)—, —O—, —S—, —S(=O)—, —S(=O)$_2$—, —$NR^3$—, —$CH_2$—$NR^3$— or —C(=O)—$NR^3$—; or a trivalent radical of formula =CH—;
—A=B— is a bivalent radical of formula —CH=CH—, —N=CH— or —CH=N—;
$R^3$ independently is hydrogen or $C_{1-6}$alkyl;
$R^4$ is hydrogen, $C_{1-6}$alkyl, $C_{3-7}$cycloalkyl or a radical of formula —Alk—$R^7$ (c-1)

or

—Alk—Z—$R^8$ (c-2);

wherein Alk is $C_{1-6}$alkanediyl;
Z is a bivalent radical of formula —O—, —S— or —$NR^3$—;
$R^7$ is phenyl; phenyl substituted with 1 or 2 substituents selected from halo, $C_{1-6}$alkyl or $C_{1-6}$alkyloxy; furanyl; furanyl substituted with 1 or 2 substituents selected from $C_{1-6}$alkyl or hydroxy$C_{1-6}$alkyl; thienyl; thienyl substituted with 1 or 2 substituents selected from halo or $C_{1-6}$alkyl; oxazolyl; oxazolyl substituted with 1 or 2 $C_{1-6}$alkyl substituents; thiazolyl; thiazolyl substituted with 1 or 2 $C_{1-6}$alkyl substituents; pyridinyl or pyridinyl substituted with 1 or 2 $C_{1-6}$alkyl substituents;
$R^8$ is $C_{1-6}$alkyl or $C_{1-6}$alkyl substituted with hydroxy, carboxyl or $C_{1-6}$alkyloxycarbonyl;
$R^5$ is hydrogen, halo, hydroxy or $C_{1-6}$alkyloxy;
$R^6$ is hydrogen, $C_{1-6}$alkyl or $Ar^1C_{1-6}$alkyl;
$Ar^1$ is phenyl; phenyl substituted with 1, 2 or 3 substituents each independently selected from halo, $C_{1-4}$alkyl, haloC$_{1-4}$alkyl, cyano, aminocarbonyl, C$_{1-4}$alkyloxy or haloC$_{1-4}$alkyloxy;

Ar$^2$ is naphtalenyl; phenyl; phenyl substituted with 1, 2 or 3 substituents each independently selected from hydroxy, halo, cyano, nitro, amino, mono- or di(C$_{1-4}$alkyl)amino, C$_{1-4}$alkyl, haloC$_{1-4}$alkyl, C$_{1-4}$alkyloxy, haloC$_{1-4}$alkyloxy, carboxyl, C$_{1-4}$alkyloxycarbonyl, aminocarbonyl and mono- or di(C$_{1-4}$alkyl)aminocarbonyl; and Het is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofubranyl and benzothienyl; each monocyclic and bicyclic heterocycle may optionally be substituted on a carbon atom by 1 or 2 substituents selected from halo, C$_{1-4}$alkyl or mono-, di- or tri(halo)methyl.

The heterocycles in the definition of Het are preferably connected to the rest of the molecule, i.e. X, —C(=Q)— or C$_{1-6}$alkyl, by a carbon atom.

As used in the foregoing definitions and hereinafter, halo is generic to fluoro, chloro, bromo and iodo; C$_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like; C$_{1-6}$alkyl is meant to include C$_{1-4}$alkyl and the higher homologues thereof having 5 to 6 carbon atoms such as, for example, pentyl, 2-methylbutyl, hexyl, 2-methylpentyl and the like; C$_{1-4}$alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl, and the like; C$_{1-6}$alkanediyl is meant to include C$_{1-4}$alkanediyl and the higher homologues thereof having form 5 to 6 carbon atoms such as, for example, 1,5-pentanediyl, 1,6-hexanediyl and the like.

As used in the foregoing definitions and hereinafter, haloC$_{1-4}$alkyl is defined as mono- or polyhalosubstituted C$_{1-4}$alkyl, in particular C$_{1-4}$alkyl substituted with 1 to 6 halogen atoms, more in particular difluoro- or trifluoromethyl.

The pharmaceutically acceptable addition salts as mentioned hereinabove are meant to comprise the therapeutically active non-toxic acid addition salt forms which the compounds of formula (I) are able to form. Said salts can conveniently be obtained by treating the base form of the compounds of formula (I) with appropriate acids such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, a metal or amine addition salt forms which the compounds of formula (I) are able to form. Said salts can conveniently be obtained by treating the compounds of formula (I) containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

For isolation and purification purposes, it is also possible to use pharmaceutically unacceptable salts. Only the pharmaceutically acceptable, non-toxic salts are used therapeutically and those salts are therefore preferred.

The term "stereochemically isomeric forms" as used hereinbefore defines all the possible isomeric as well as conformational forms which the compounds of formula (I) may possess. Unless otherwise mentioned or indicated, the chemical designation of compounds denotes the mixture, more in particular the racemic mixture, of all possible stereochemically and conformationally isomeric forms, said mixtures containing all diastereomers, enantiomers and/or conformers of the basic molecular structure. More in particular, stereogenic centers may have the R- or S-configuration; substituents on bivalent cyclic saturated radicals may have either the cis- or trans-configuration; >C=NR$^3$ and C$_{3-6}$alkenyl radicals may have the E- or Z-configuration. For the compounds having two stereogenic centers, the relative stereodescriptors R* and S* are used in accordance with the Chemical Abstracts rules (Chemical Substance Name Selection Manual (CA), 1982 Edition, Vol. III, Chapter 20). All stereochemically isomeric forms of the compounds of formula (I) both in pure form or mixtures thereof are intended to be embraced within the scope of the present invention.

Some of the compounds of formula (I) may also exist in their tautomeric form. Such forms although not explicitly indicated in the above formula are intended to be included within the scope of the present invention. For instance, compounds of formula (I) wherein X is —NH— and =Q is =O and compounds of formula (I) wherein Y— is —C(=O)—NH— may exist in their corresponding tautomeric form.

The N-oxide forms of the compounds of formula (I) are meant to comprise those compounds of formula (I) wherein one or several nitrogen atoms are oxidized to the so-called N-oxide, particularly those N-oxides wherein one or more of the piperazine-nitrogens are N-oxidized.

Whenever used hereinafter, the term "compounds of formula (I)" is meant to also include their N-oxide forms, their pharmaceutically acceptable addition salts, and their stereochemically isomeric forms.

An important group of compounds are those compounds of formula (I) wherein L is a radical of formula (A) and Het is a monocyclic heterocycle selected from pyrrolyl, pyrazolyl, imidazolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, C$_{1-4}$alkyl or mono-, di- or tri(halo)methyl.

Another important group of compounds are those compounds of formula (I) wherein L is a radical of formula (B) and Het is a monocyclic heterocycle selected from pyrrolyl, pyrazolyl, imidamolyl, furanyl, thienyl, oxazolyl, isoxazolyl, thiazolyl, isothiazolyl, pyridinyl, pyrimidinyl, pyrazinyl and pyridazinyl; or a bicyclic heterocycle selected from quinolinyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl or mono-, di- or tri(halo)methyl.

A first group of interesting compounds consists of those compounds of formula (I) wherein one or more of the following restrictions apply:

a) $R^1$ is $Ar^1$ or $Ar^1C_{1-6}$alkyl; or b) $R^2$ is phenyl$C_{1-6}$alkyl; quinolinyl; quinoxalinyl; optionally substituted isoxazolyl; optionally substituted pyridinyl; optionally substituted thiazolyl; optionally substituted pyrazinyl; optionally substituted benzofuranyl; benzothiazolyl; optionally substituted indolyl; optionally substituted pyrrolyl; thienyl; furanyl; naphtalenyl; phenyl; phenyl substituted with 1, 2 or 3 substituents each independently selected from amino, halo, cyano, $C_{1-4}$alkyl, $C_{1-4}$alkyloxy and halo$C_{1-4}$alkyl, in particular, selected from methyl and trifluoromethyl; or c) n is 1 or 2; or d) m is 1 or 2; or e) =Q is =O; or f) X is a covalent bond, —S—, —NH— or —O—.

A second group of interesting compounds consists of those compounds of formula (I) wherein .....Y— is —NR$^3$—, —CH$_2$—, —CH(OH)—, —S—, —S(=O)— or —O—; —A=B— is —CH=CH— or —N=CH—; $R^4$ is $C_{1-6}$alkyl; or $R^4$ is a radical of formula (c-1) wherein $R^7$ is phenyl substituted with halo or $C_{1-6}$alkoxy; thienyl; thiazolyl optionally substituted with $C_{1-6}$alkyl; oxazolyl optionally substituted with 1 or 2 $C_{1-6}$alkyl substituents; furanyl optionally substituted with $C_{1-6}$alkyl or hydroxy$C_{1-6}$alkyl; or $R^4$ is a radical of formula (c-2) wherein Z is a bivalent radical of formula —O—, and $R^8$ is $C_{1-6}$alkyl; $R^5$ is hydrogen; and $R^6$ is hydrogen or $Ar^1C_{1-6}$alkyl.

Of special interest are those compounds of formula (I) wherein $R^1$ is $Ar^1C_{1-6}$alkyl, $R^2$ is phenyl substituted with 2 substituents selected from methyl or trifluoromethyl, X is a covalent bond and =Q is =O.

Further of special interest are those compounds of formula (I) wherein L is a radical of formula (A) and p is 0 or 1.

Also of special interest are those compounds of formula (I) wherein L is a radical of formula (B), n is 1 or 2, and m is 1 or 2, provided that if m is 2, then n is 1.

A particular group of compounds consists of those compounds of formula (I) wherein $R^1$ is phenylmethyl; $R^2$ is phenyl substituted with 2 substituents selected from methyl or trifluoromethyl; n, m are 1; X is a covalent bond; and =Q is =O.

Another particular group of compounds consists of those compounds of formula (I) wherein .....Y— is —NH— or —O—; —A=B— is —CH=CH— or —N=CH—; $R^4$ is a radical of formula (c-1) wherein $R^7$ is oxazolyl substituted with 1 or 2 $C_{1-6}$alkyl substituents, furanyl substituted with $C_{1-6}$alkyl or hydroxy$C_{1-6}$alkyl; or $R^4$ is a radical of formula (c-2) wherein Z is a bivalent radical of formula —O—, and $R^8$ is $C_{1-6}$alkyl; $R^5$ is hydrogen; and $R^6$ is hydrogen.

Preferred compounds are those compounds of formula (I) wherein $R^1$ is phenylmethyl; $R^2$ is phenyl substituted with 2 substituents selected from methyl or trifluoromethyl; n, m are 1; X is a covalent bond; and =Q is =O; .....Y— is —NH—; —A=B— is —CH=CH— or —N=CH—; $R^4$ is a radical of formula (c-1) wherein Alk is methylene; and $R^7$ is oxazolyl substituted with 1 or 2 methyl substituents, furanyl substituted with methyl or hydroxymethyl; or $R^4$ is a radical of formula (c-2) wherein Alk is ethanediyl; Z is a bivalent radical of formula —O—, and $R^8$ is ethyl; $R^5$ is hydrogen; and $R^6$ is hydrogen.

Most preferred are

1-[1,3-bis(trifluoromethyl)benzoyl]-4-[4-[[1-(2-ethoxyethyl)-1H-benzimidazol-2-yl]amino]-1-piperidinyl]-2-(phenylmethyl)piperidine;

1-[3,5-bis(trifluoromethyl)benzoyl]-4-[4-[[1-[(2-methyl-5-oxazolyl)methyl]-1H-benzimidazol-2-yl]amino]-1-piperidinyl]-2-(phenylmethyl)piperidine;

1-[3,5-bis(trifluoromethyl)benzoyl]-4-[4-[[3-(5-methyl-2-furanyl)-3H-imidazo[4,5-b]-pyridin-2-yl]amino]-1-piperidinyl]-2-(phenylmethyl)piperidine;

1-[3,5-bis(trifluoromethyl)benzoyl]-4-[3-[[3-[(5-methyl-2-furanyl)methyl]-3H-imidazo-[4,5-b]pyridin-2-yl]amino]-1-pyrrolidinyl]-2-(phenylmethyl)piperidine;

1-[3,5-bis(trifluoromethyl)benzoyl]-4-[4-[[1-[(5-methyl-2-furanyl)methyl]-1H-benzimidazol-2-yl]amino]-1-piperidinyl]piperidine;

1-[3,5-bis(trifluoromethyl)benzoyl]-4-[[1-(2-ethoxyethyl)-1H-benzimidazol-2-yl]-amino]-2-(phenylmethyl)piperidine;

1-[3,5-bis(trifluoromethyl)benzoyl]-4-[[1-[(2-methyl-4-oxazolyl)methyl]-1H-benzimidazol-2-yl]amino]-2-(phenylmethyl)piperidine;

1-[3,5-bis(trifluoromethyl)benzoyl]-4-[[1-[(5-methyl-2-furanyl)methyl]-1H-benzimidazol- 2-yl]amino]-2-(phenylmethyl)piperidine; the stereoisomeric forms and the pharmaceutically acceptable acid addition salts thereof.

The compounds of formula (I) can generally be prepared by reacting an intermediate of formula (II) wherein $W^1$ is an appropriate leaving group such as, for example, a halogen, e.g. chloro or bromo, or a sulfonyloxy leaving group, e.g. methanesulfonyloxy or benzenesulfonyloxy, with an intermediate of formula (III). The reaction can be performed in a reaction-inert solvent such as, for example, a chlorinated hydrocarbon, e.g. dichloromethane, an alcohol, e.g. ethanol, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried at a temperature ranging between room temperature and reflux temperature.

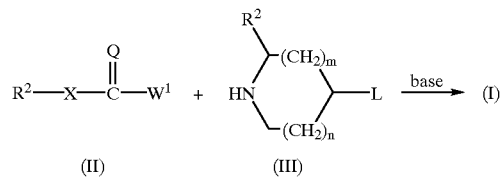

Alternatively and under similar reaction conditions, intermediates of formula (II) wherein =Q is =O may be replaced by functional derivatives thereof such as, for example, anhydrides, e.g. isatoic anhydride, thus forming compounds of formula (I) wherein Q is oxygen, said compounds being represented by formula (I-1).

In this and the following preparations, the reaction products may be isolated from the reaction medium and, if necessary, further purified according to methodologies generally known in the art such as, for example, extraction, crystallization, trituration and chromatography.

The compounds of formula (I) wherein L is a radical of formula (A), said compounds being referred to as (I-A), can be prepared by reductively N-alkylating an intermediate of formula (V) with an intermediate of formula (IV). Said reductive N-alkylation may be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. In case a borohydride is used as a reducing agent, it may be convenient to use a catalyst such as, for example, titanium(IV) isopropylate as described in J. Org. Chem, 1990, 55, 2552–2554. Using said catalyst may also result in an improved cis/trans ratio in favour of the trans isomer. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. Stirring and optionally elevated temperatures and/or pressure may enhance the rate of the reaction.

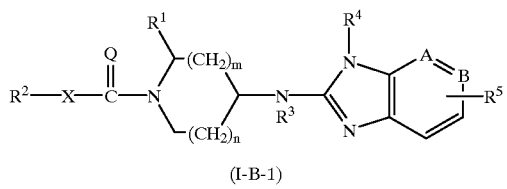

(I-B-1)

Alternatively, compounds of formula (I-B-1) may also be prepared by reacting an intermediate of formula (VII) with an intermediate of formula (VIII) wherein $W^2$ is an appropriate leaving group such as, for example, a halogen, e.g. chloro, in the presence of a suitable catalyst such as, for example, copper. The reaction may be performed in a reaction-inert solvent such as, for example, N,N-dimethylformamide. However, it is convenient to perform said reaction without solvent at a temperature just above the melting point of the reagents. Stirring enhances the rate of the reaction.

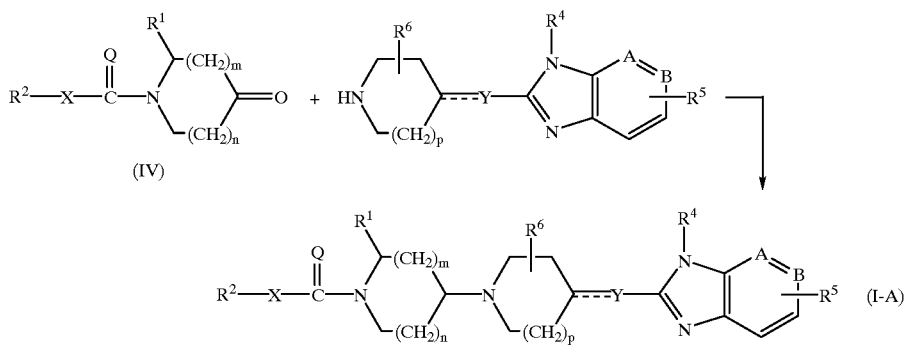

The compounds of formula (I) wherein L is a radical of formula (B) and ⁼⁼⁼Y— is —NR³—, said compounds being represented by formula (I-B-1), can be prepared by reductively N-alkylating an intermediate of formula (VI) with an intermediate of formula (IV). Said reductive N-alkylation may be performed in a similar way to the reductive N-alkylation procedure described hereinabove.

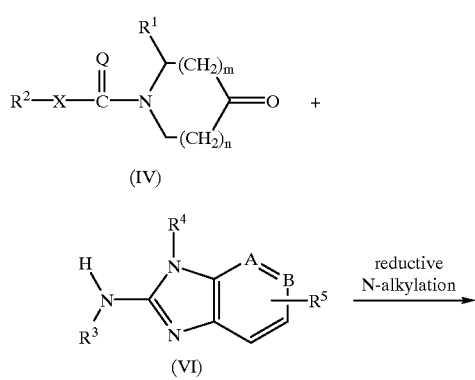

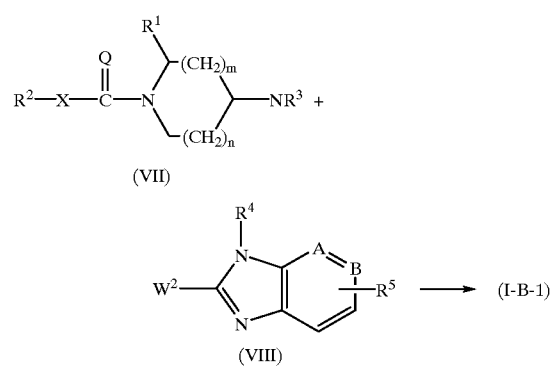

The compounds of formula (I) wherein L is a radical of formula (B) and ⁼⁼⁼Y— is —S— said compounds being represented by formula (I-B-2), can be prepared by reacting an intermediate of formula (IX) wherein $W^3$ is a suitable leaving group such as, for example, a sulfonyloxy leaving group, e.g. methanesulfonyloxy or benzenesulfonyloxy, with an intermediate of formula (X). Said reaction may be performed using a similar reaction procedure as for the preparation of compounds of formula (I) form intermediates (II) and (III).

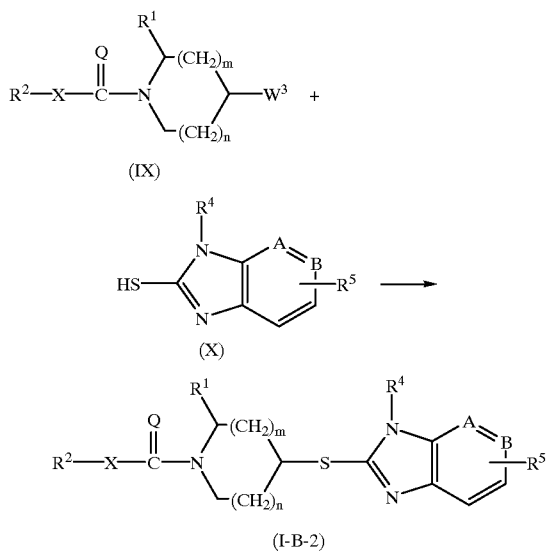

The compounds of formula (I) wherein L is a radical of formula (B) and ....Y— is —O—, said compounds being represented by formula (I-B-3), can be prepared by reacting an intermediate of formula (XI) with an intermediate of formula (VIII).The reaction may be performed in a reaction-inert solvent such as, for example, N,N-dimethylformamide and in the presence of a suitable base such as, for example, sodium hydride. Stirring and temperatures up to reflux temperature may enhance the rate of the reaction.

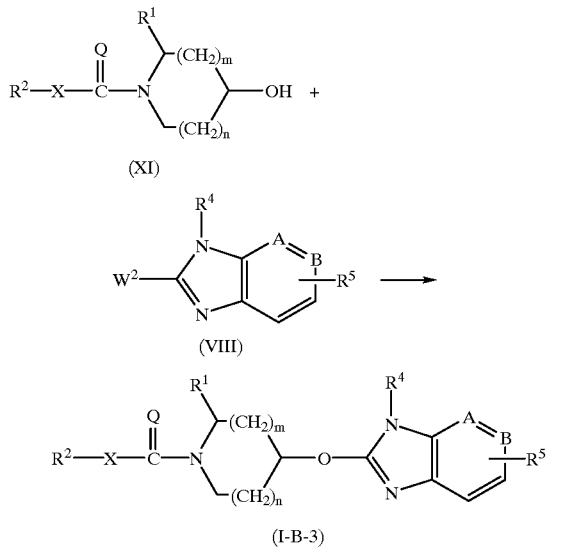

The compounds of formula (I) may be converted into each other following art-known transformations. For instance, compounds of formula (I-B- 1) wherein $R^3$ is hydrogen may be converted into their corresponding N-alkyl derivatives using a suitable alkylating agent such as, for example, an alkyliodide, e.g. methyl iodide, in the presence of a suitable base such as, for example, sodium hydride.

Also, compounds of formula (I-B-2) may be converted to their corresponding sulfoxides using a suitable oxidizing agent such as, for example, 3-chlorobenzene-carboperoxoic acid.

The compounds of formula (I) may be converted into each other following art-known transformations. The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art. For example, intermediates of formula (III) wherein L is a radical of formula (B) and intermediates of formula (V) may be prepared as described in EP-0,378,254-A, WO 92/06086, W093/14083, EP-0,539, 421-A and EP-0,539,420-A In particular, intermediates of formula (III) wherein L is a radical of formula (B) and ....Y— is —$NR^3$—, said intermediates being represented by formula (III-B- 1), may be prepared by first reacting an intermediate of formula (XII) wherein $P^1$ is a suitable protecting group such as for example, phenylmethyl or a $C_{1-6}$alkyloxycarbonyl group, with an intermediate of formula (VIII) using the same reaction procedure as for the preparation of compounds of formula (I-a) from intermediates (VII) and (VIII); and subsequently deprotecting the thus formed intermediate using art-known deprotection techniques.

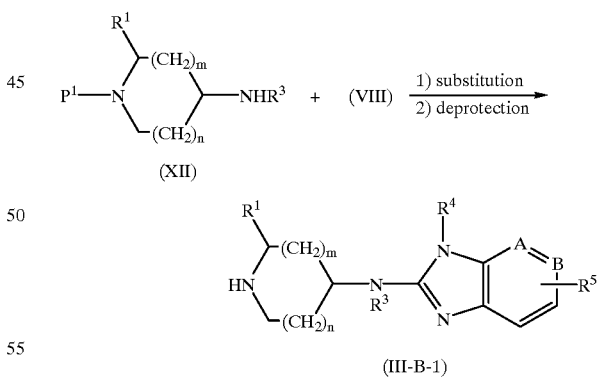

Alternatively, intermediates of formula (III-B-1) may also be prepared by reductively N-alkylating an intermediate of formula (VI) with an intermediate of formula (XIII) wherein $P^1$ is a suitable protecting group such as for example, phenylmethyl or a $C_{1-6}$alkyloxycarbonyl group, using the same reaction procedure as for the preparation of compounds of formula (I-B-1) from intermediates (IV) and (VI); and subsequently deprotecting the thus formed intermediate using art-known deprotection techniques.

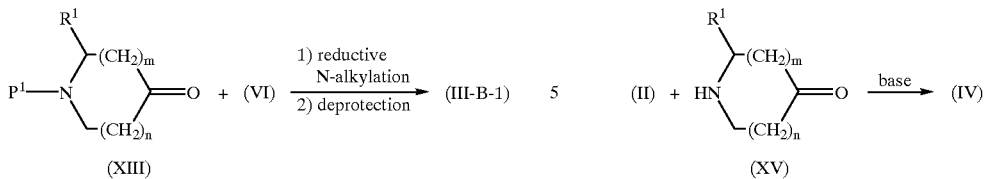

Intermediates of formula (III) wherein L is a radical of formula (B) and ┄┄Y— is —O—, said intermediates being represented by formula (III-B-3), may be prepared by first reacting an intermediate of formula (XIV) wherein $P^1$ is a suitable protecting group such as for example, phenylmethyl or a $C_{1-6}$alkyloxycarbonyl group, with an intermediate of formula (VIII) using the same reaction procedure as for the preparation of compounds of formula (I-B-3) from intermediates (XI) and (VIII); and subsequently deprotecting the thus formed intermediate using art-known deprotection techniques.

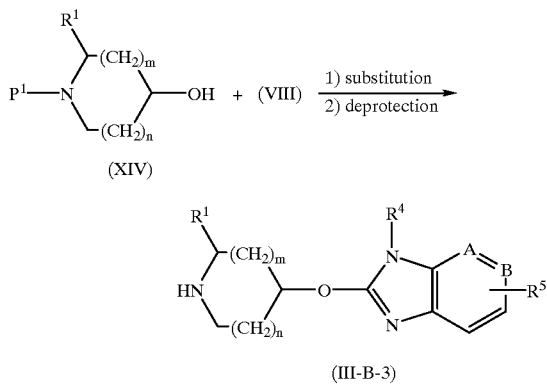

Intermediates of formula (IV) may be prepared by condensing an intermediate of formula (II) with an intermediate of formula (XV) in an analogous way as described in EP-0,532,456-A.

Ways to prepare intermediates of formula (XV) are also described in EP-0,532,456-A. However, intermediates of formula (XV) wherein $R^1$ is optionally substituted $Ar^1C_{1-6}$alkyl or di($Ar^1$)$C_{1-6}$alkyl, said $R^1$ being represented by —CH($R^{1a}$)$_2$ and said intermediates being represented by formula (XV-a), may also be prepared as depicted in scheme 1.

Scheme 1

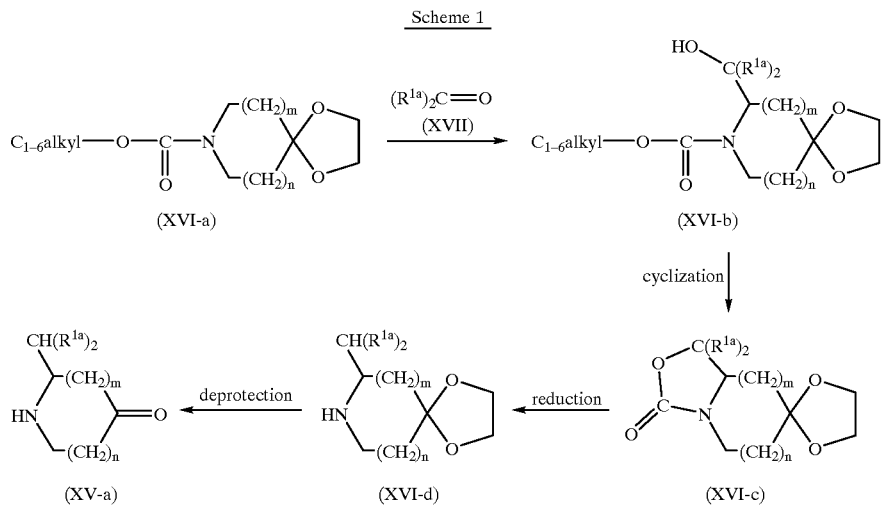

In scheme 1, the intermediates of formula (XVI-b) may be prepared by reacting an intermediate of formula (XVI-a) with an aldehyde or a ketone of formula (XVII). The $C_{1-6}$alkylcarbamate moiety in the intermediates of formula (XVI-b) may be converted into a fused oxazolone which in turn may be reduced to an intermediate of formula (XVI-d). Said intermediate (XVI-d) may in turn be deprotected, thus forming an intermediate of formula (XV-a). Subsequently, intermediates of formula (XV-a) may be reacted with an intermediate of formula (II) to prepare intermediates of formula (IV) wherein $R^1$ is defined as —CH($R^{1a}$)$_2$, said intermediates being represented by formula (IV-a). The reactions performed in scheme 1 may all be conducted following conventional methods that are generally known in the art.

Intermediates of formula (XV) wherein n and m are 1 and $R^1$ is $Ar^1$, said intermediates being represented by formula (XV-b), may be prepared by reacting a benzaldehyde of formula (XVIII) with an intermediate of formula (XIX) or a functional derivative thereof, and subsequently deprotecting the resulting ketalized 4-piperidinone derivative using art-known deprotection techniques. Said reaction may be performed in a reaction-inert solvent such as, for example, toluene, and in the presence of an acid such as, for example, p-toluenesulfonic acid.

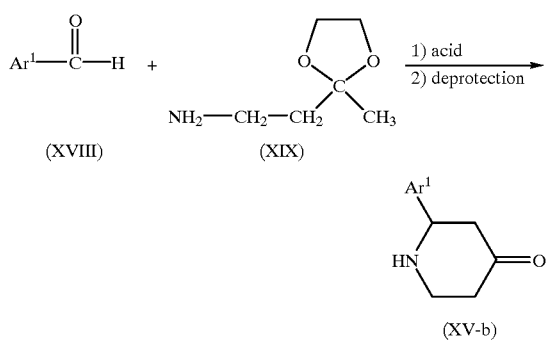

Intermediates of formula (III) wherein L is a radical of formula (A), said intermediates being represented by formula (III-A), may suitably be prepared by reacting an intermediate of formula (XIII) with an intermediate of formula (V) according to the previously described reductive N-alkylation procedure, and subsequently deprotecting the thus formed intermediate.

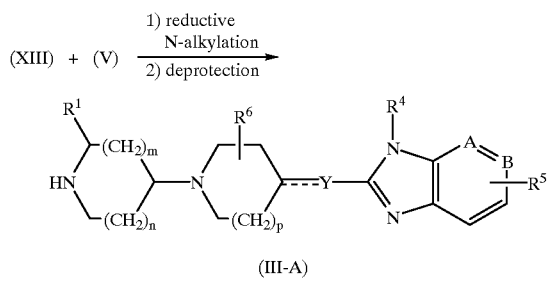

In particular, intermediates of formula (III-A) wherein $R^1$ is $-CH(R^{1a})_2$, said intermediates being represented by formula (III-A-1), may be prepared as is depicted in scheme 2.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereo-specifically. Preferably if a specific stereoisomer is desired, said compound will be synthesized by stereospecific methods of preparation. These methods will advantageously employ enantiomerically pure starting materials.

The compounds of formula (I) have valuable pharmacological properties in that they interact with tachykinin receptors and they antagonize tachykinin-induced effects, especially substance P-induced effects, both in vivo and in vitro and are thus of use in the treatment of tachykinin-mediated diseases, and in particular in substance P-mediated diseases.

Tachykinins, also referred to as neurokinins, are a family of peptides among which substance P (SP), neurokinin A (NKA), neurokinin B (NKB) and neuropeptide K (NPK) may be identified. They are naturally occurring in mammals, including human beings, and are distributed throughout the central and peripheral nervous system, where they act as

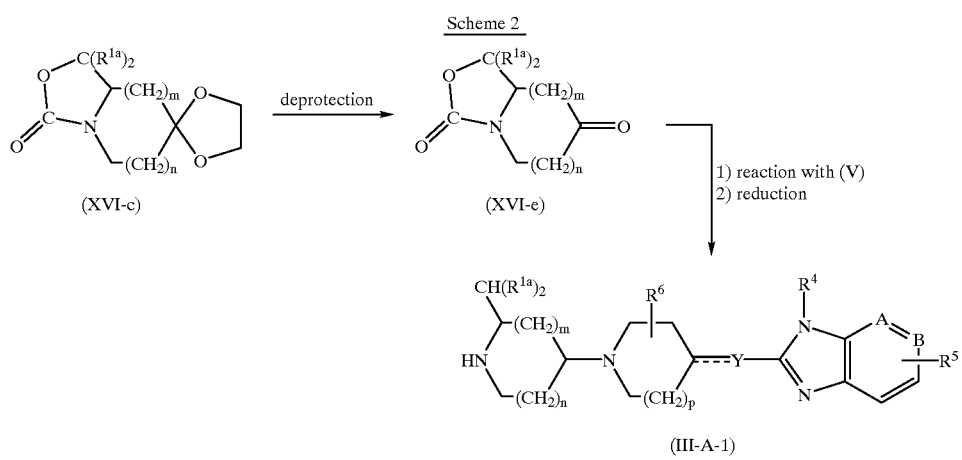

The ketalized intermediate of formula (XVI-c) may be transformed to the corresponding ketone of formula (XVI-e) which subsequently may be reductively aminated with a pyrrolidine, piperidine- or homopiperidine derivative of formula (V). The thus obtained intermediate may then be reduced with a suitable reducing agent to an intermediate of formula (III-A-1).

neurotransmitters or neuromodulators. Their actions are mediated through several subtypes of receptors, such as, for example, $NK_1$, $NK_2$ and $NK_3$ receptors. Substance P displays highest affinity for $NK_1$ receptors, whereas NKA preferentially,, binds to $NK_2$ receptors and NKB preferentially binds to $NK_3$ receptors. However, the selectivity of these tachykinins is relatively poor and under physiological conditions the action of any of these tachykinins might be mediated by activation of more than one receptor type.

Substance P and other neurokinins are involved in a variety of biological actions such as pain transmission (nociception), neurogenic inflammation, smooth muscle contraction, plasma protein extravasation, vasodilation, secretion, mast cell degranulation, and also in activation of the immune system. A number of diseases are deemed to be engendered by activation of neurokinin receptors, in particular the $NK_1$ receptor, by excessive release of substance P and other neurokinins in particular cells such as cells in the neuronal plexi of the gastrointestinal tract, unmyelinated primary sensory afferent neurons, sympathetic and parasympathetic neurons and nonneuronal cell types (DN&P 8(1), February 1995, p. 5–23, "Neurokinin Receptors" by Longmore J. et al.; Pharmacological Reviews 46(4), 1994, p. 551–599, "Receptors and Antagonists for Substance P and Related Peptides" by Regoli et al.).

The compounds of the present invention are potent inhibitors of neurokinin-mediated effects, in particular those mediated via the $NK_1$ receptor, and may therefore be described as tachykinin antagonists, especially as substance P antagonists, as indicated in vitro by the antagonism of substance P-induced relaxation of pig coronary arteries which is described hereinafter. The binding affinity of the present compounds for the human, guinea-pig and gerbil neurokinin receptors may be determined in vitro in a receptor binding test using $^3$H-substance P as radioligand. The subject compounds also show substance-P antagonistic activity in vivo as may be evidenced by, for instance, the antagonism of substance P-induced plasma extravasation in guinea-pigs.

In view of their capability to antagonize the actions of tachykinins by blocking the tachykinin receptors, and in particular antagonizing the actions of substance P by blocking the $NK_1$ receptor, the subject compounds are useful in the prophylactic and therapeutic treatment of tachykinin-mediated diseases such as, for example, pain, in particular traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS-related neuropathy, occipital neuralgia, geniculate neuralgia, glossopharyngeal neuralgia, reflex sympathetic dystrophy, phantom limb pain; various forms of headache such as migraine, acute or chronic tension headache, temperomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain;

respiratory and inflammatory diseases, in particular inflammation in asthma, influenza, chronic bronchitis and rheumatoid arthritis; inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation;

emesis, i.e. nausea, retching and vomiting, including acute emesis, delayed emesis and anticipatory emesis, no matter how emesis is induced, for example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia;

central nervous system disorders, in particular psychoses such as schizophrenia, mania, dementia or other cognitive disorders e.g. Alzheimer's disease; anxiety; AIDS-related dementia; diabetic neuropathy; multiple sclerosis; depression; Parkinson's disease; and dependence on drugs or substances of abuse;

allergic disorders, in particular allergic disorders of the skin such as urticaria, and allergic disorders of the airways such as rhinitis;

gastrointestinal disorders, such as irritable bowel syndrome;

skin disorders, such as psoriasis, pruritis and sunburn;

vasospastic diseases, such as angina, vascular headache and Reynaud's disease;

cerebral ischaemia, such as cerebral vasospasm following subarachnoid haemorrhage stroke, epilepsie, head trauma, spinal cord trauma and ischemic neuronal damage;

fibrosing and collagen diseases, such as scleroderma and eosinophilic fascioliasis;

disorders related to immune enhancement or suppression, such as systemic lupus erythematosus;

rheumatic diseases, such as fibrositis;

neoplastic disorders;

cell proliferation; and cough.

The compounds of the present invention have a favourable metabolic stability and exhibit good oral availability. They also have an advantageous onset and duration of action.

In view of the utility of the compounds of formula (I), there is provided a method of treating warm-blooded animals, including humans, suffering from tachykinin-mediated diseases as mentioned hereinabove, in particular, asthma. Said method comprises the systemic administration of an effective tachykinin antagonizing amount of a compound of formula (I), a N-oxide form, a pharmaceutically acceptable addition salt or a possible stereoisomeric form thereof, to warm-blooded animals, including humans. Hence, the use of a compound of formula (I) as a medicine is provided, and in particular a medicine to treat asthma.

For ease of administration, the subject compounds may be formulated into various pharmaceutical forms for administration purposes. To prepare the pharmaceutical compositions of this invention, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action.

Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid or base addition salts of compounds of formula (I) due to their increased water solubility over the corresponding base or acid form, are obviously more suitable in the preparation of aqueous compositions.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxy-propyl-β-cyclodextrin. Also co-solvents such as alcohols may improve the solubility and/or the stability of the compounds of formula (I) in pharmaceutical compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those of skill in the treatment of tachykinin mediated diseases could determine the effective therapeutic daily amount from the test results presented hereinafter. An effective therapeutic daily amount would be from about 0.001 mg/kg to about 40 mg/kg body weight, more preferably from about 0.01 mg/kg to about 5 mg/kg body weight. It may be appropriate to administer the therapeutically effective dose once daily or as two, three, four or more sub-doses at appropriate intervals throughout the day. Said sub-doses may be formulated as unit dosage forms, for example, containing 0.05 mg to 500 mg, and in particular, 0.5 mg to 50 mg of active ingredient per unit dosage form.

The exact dosage and frequency of administration depends on the particular compound of formula (1) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines.

The following examples are intended to illustrate and not to limit the scope of the present invention.

EXPERIMENTAL PART

Hereinafter, "DIPE" means diisopropylether, "RT" means room temperature. Of some compounds of formula (I) the absolute stereochemical configuration was not experimentally determined. In those cases the stereochemically isomeric form which was first isolated is designated as "A" and the second as "B", without further reference to the actual stereochemical configuration.

A. PREPARATION OF THE INTERMEDIATES

EXAMPLE A1

A mixture of (±)-1,1-dimethylethyl 7-(phenylmethyl)-1,4-dioxo-8-azaspiro[4.5]-decane-8-carboxylate (33.34 g) in HCl (6N; 250 ml) was stirred at 70° C. for 1.5 hour. The mixture was cooled, $CH_2Cl_2$ (100 ml) was added and NaOH was added while cooling to RT. The organic layer was separated and the aqueous layer was extracted with $CH_2Cl_2$. Triethylamine (20.2 g), followed by 3,5-bis (trifluoromethyl)-benzoylchloride (27.7 g) dissolved in $CH_2Cl_2$ were added and the mixture was stirred for 2 hours. Water was added and the layers were separated. The organic layer was dried, filtered and the solvent evaporated. The residue was crystallized from DIPE, the precipitate was filtered off and dried, yielding 18.34 g of fraction 1. The solvent of the mother layer was evaporated and the residue was crystallized from DIPE. The precipitate was filtered off and dried, yielding 6.51 g of fraction 2. The two fractions were put together and taken up in water and $CH_2Cl_2$. NaOH was added and the mixture was extracted. The organic layer was dried, filtered and the solvent evaporated, yielding 16.14 g (38%) of (±)-1-[3,5-bis(trifluoromethyl)benzoyl]-2-(phenylmethyl)-4-piperidinone (interm. 1; mp. 102.5° C.).

EXAMPLE A2 a) A mixture of (±)-1,1-dimethylethyl 7-(hydroxyphenylmethyl)-1,4-dioxa-8-azaspiro[4.5]decane-8-carboxylate (183.6 g) and potassium tert-butoxide (6 g) in toluene (900 ml) was stirred and refluxed for 2 hours. The solvent was evaporated and the residue was stirred in petrol ether and water. The mixture was decanted and the residue was stirred up in DIPE. The precipitate was filtered off and dried, yielding 127.4 g (92%) of (±)-tetrahydro-1'-phenylspiro(1,3-dioxolan-2,7'(8'H)-3H-oxazolo[3,4-a]pyridin)-3'-one (interm. 2).

b) A mixture of intermediate (2) (137 g) in methanol (700 ml) was hydrogenated at 50° C. overnight with palladium on activated carbon (10%; 5 g) as a catalyst. After uptake of hydrogen, the catalyst was filtered off and the filtrate was evaporated. The residue was taken up in water and extracted with $CH_2Cl_2$. The organic layer was dried, filtered and the solvent evaporated, yielding 99 g (85%) of (±)-7-(phenylmethyl)-1,4-dioxa-8-azaspiro[4.5]decane (interm 3).

c) A mixture of intermediate (3) (13 g) in HCl (6N; 130 ml) was stirred and refluxed for 3 hours. The mixture was cooled, decanted, alkalized with NaOH 50% and extracted with $CH_2Cl_2$. The organic layer was dried and filtered, yielding (±)-7-(phenylmethyl)-1,4-dioxa-8-azaspiro[4.5]decane in $CH_2Cl_2$ (interm. 4).

d) A mixture of intermediate (4), 3,5-dimethylbenzoylchloride (7.4 g) and triethylamine (11 ml) was stirred overnight at RT. The reaction mixture was washed with dilute NaOH and the organic layer was separated, dried, filtered and the solvent evaporated. The residue was crystallized from DIPE. The precipitate was filtered off and dried, yielding 7.44 g (58%) of (±)-1-(3,5-dimethylbenzoyl)-2-(phenylmethyl)-4-piperidinone (interm. 5; mp. 107.8° C.).

EXAMPLE A3 a) (±)-1,1-dimethylethyl trans-4-amino-2-(phenylmethyl)-1-piperidinecarboxylate (5 g), 1-(2-ethoxyethyl)-2-chloro-1H-benzimidazole (4.5 g) and copper (1.28 g) were stirred at 150° C. for 4 hours. The mixture was taken up in $CH_2Cl_2$ and filtered. The filtrate was washed with water/$NH_3$. The organic layer was dried, filtered and the solvent evaporated. The residue was purified by column chromatography over silica gel (eluent: $CH_2Cl_2$/($CH_3OH$/$NH_3$) 98/2). The pure fractions were collected and the solvent evaporated, yielding 6 g (73.7%) of (±)-1,1-dimethylethyl trans-4-[[1-(2-ethoxyethyl)-1H-benzimidazol-2-yl]amino]-2-(phenylmethyl)-1-piperidine-carboxylate (interm. 6).

b) Intermediate (6) (6 g) was taken up in methanol (160 ml). HCl in 2-propanol (16 ml) was added and the mixture was stirred and refluxed for 1 hour. The solvent was evaporated, the residue was taken up in diluted NaOH, and extracted with $CH_2Cl_2$. The organic layer was separated and purified on a glass filter over silica gel (eluent: $CH_2Cl_2$/($CH_3OH$/$NH_3$) 95/5). The pure fractions were collected and evaporated. The residue was crystallized from DIPE, yielding 3 g (63.4%) of (±)-trans-1-(2-ethoxy-ethyl)-N-[2-(phenylmethyl)-4-piperidinyl]-1H-benzimidazol-2-amine (interm. 7).

EXAMPLE A4 a) 1,1-dimethylethyl 1,3-dioxa-8-azaspiro[4.5]decane-8-carboxylate (24.3 g) in diethyl ether (150 ml) and N,N,N',N'-tetramethylethylenediamine (32 ml) was stirred and cooled under $N_2$ on a 2-propanol/$CO_2$ bath. sec-buthyllithium (1.4M; 85.7 ml) was added dropwise at a temperature below −60° C. and the mixture was stirred at −60° C. for 3 hours. 3,4-Dimethoxybenzaldehyde (19.94 g) in sec-buthyllithium was added and the mixture was stirred at −60° C. for 1 hour. The mixture was brought to RT and stirred overnight. The mixture was decomposed with water, DIPE was added and the ether layer was decanted twice. The precipitate and the aqueous layers were extracted with $CH_2Cl_2$. The organic layer was separated, dried, filtered and the solvent evaporated. The residue was crystallized from DIPE and the precipitate was filtered off, yielding 2.7 g (8%) of (±)-1-(3,4-dimethoxyphenyl)tetrahydrospiro[1,3-dioxolane-2,7'(1'H)-oxazolo[3,4-a]pyridin]-3'(3'H)-one (interm. 8; mp. 162.6° C.).

b) Trifluoroacetic acid (5 ml) was added to a mixture of intermediate (8) (1 g) in $CH_2Cl_2$ (25 ml) and the mixture was stirred at RT for a few hours. The mixture was poured into alkalic water and extracted with $CH_2Cl_2$. The organic layer was separated, dried, filtered and the solvent evaporated. The residue was suspended in DIPE, filtered off and dried. The residue was recrystallized from $CH_3CN$, filtered off and dried, yielding 0.19 g of (±)-1-(3,4-dimethoxyphenyl)tetrahydro-3H-oxazolo[3,4-a]pyridine-3,6(1H)-dione (interm. 9; mp. 180.2° C.).

c) A solution of intermediate (9) (9 g) in methanol (250 ml) was hydrogenated at 50° C. with palladium on activated carbon (10%; 3 g) as a catalyst. After uptake of hydrogen, the catalyst was filtered off and the solvent was evaporated. The residue was purified by column chromatography over silica gel (eluent: $CH_2Cl_2$/($CH_3OH$/$NH_3$ 7N) 95/5). The pure fractions were collected and evaporated, yielding 3 g (40%) of (±)-2-[(3,4-dimethoxyphenyl)methyl]-4-piperidinone (interm 10).

EXAMPLE A5 a) A solution of benzaldehyde (10.6 g) and 2-methyl-1,3-dioxolane-2-ethanamine (13.1 g) in toluene (100 ml) was stirred for 16 hours at RT. This solution was added at 100° C. to a solution of 4-methylbenzenesulfonic acid (34.4 g) in toluene (100 ml) and the mixture was stirred for 1 hour at 100° C. The mixture was poured into an ice/water bath, $K_2CO_3$ was added to a pH of about 8 and extracted with ethyl acetate. The organic layer was dried, filtered and the solvent evaporated, yielding 14.3 g (70%) of (±)-7-phenyl-1,3-dioxa-8-azaspiro[4.5]decane (interm. 11).

b) A mixture of intermediate (11) (14.5 g) in HCl (6N; 150 ml) was stirred and heated at 60° C. for a few hours. The mixture was cooled, poured into a saturated $K_2CO_3$ solution and extracted with $CH_2Cl_2$. The organic layer was dried, filtered and the solvent was evaporated. The residue was purified by column chromatography over silica gel (eluent: $CH_2Cl_2$/$CH_3OH$—$NH_3$ 95/5). The pure fractions were collected and evaporated, yielding 7.3 g (57%) (±)-2-phenyl-4-piperidinone (interm. 12).

EXAMPLE A6 a) Iodine (crystals) was added to magnesium turnings (8.63 g) in diethyl ether under $N_2$. Benzyl bromide was added and the Grignard reaction was started. Benzyl bromide (60.65 g) in diethyl ether (443 ml) was added dropwise at reflux temperature while stirring, the reaction mixture was refluxed for 1 hour. The Grignard reagens was added dropwise to a suspension of 4-methoxy-1-(phenylmethyl) pyridinium bromide (75 g) in diethyl ether (1200 ml) and the mixture was stirred at RT for 18 hours. The mixture was poured into HCl (12M; 150 ml) and water (600 ml), alkalized with $NH_4OH$ and NaOH and extracted with $CH_2Cl_2$. The combined organic layers were washed with water, dried, filtered and the solvent was evaporated, yielding 76 g (100%) of (±)-1,2-dihydro-4-methoxy-1,2-bis(phenylmethyl)pyridine (interm 13).

b) NaOH (370 ml) was added to intermediate (13) (76 g) in methanol (1100 ml) and the mixture was stirred and refluxed for 1.5 hours. The solvent was evaporated and the residue was extracted with CH$_2$Cl$_2$. The organic layer was washed with water, dried, filtered and the solvent evaporated. The residue was purified by column chromatography over silica gel (eluent: CH$_2$Cl$_2$/CH$_3$OH 95/5). The pure fractions were collected and the solvent evaporated. The residue was taken up in toluene, filtered and the solvent evaporated, yielding 40 g (54.3%) of (±)-2,3-dihydro-1,2-bis(phenylmethyl)-4(1H)-pyridinone (interm. 14).

c) Intermediate (14) (40 g) was hydrogenated in methanol (600 ml) with Raney nickel (5 g) as a catalyst. After uptake of hydrogen, the catalyst was filtered off and the solvent was evaporated. The residue was purified by column chromatography over silica gel (eluent: CH$_2$Cl$_2$/(CH$_3$OH/NH$_3$) 95/5). The pure fractions were collected and the solvent evaporated. The residue was crystallized from CH$_3$CN, yielding 5.4 g (19.6%) of (±)-cis-2-(phenylmethyl)-4-piperidinol (interm. 15; mp. 113.9° C.).

EXAMPLE A7

A mixture of intermediate (10) (2.8 g) in CH$_2$Cl$_2$ (50 ml) was stirred and 3,5-bis(trifluoromethyl)benzoyl chloride (3.32 g) was added. While stirring, triethylamine (2.8 ml) was added and the mixture was stirred at RT for 3 hours. The mixture was washed with diluted NaOH 50%, then with water, dried, filtered and the solvent was evaporated. The residue was purified by column chromatography over silica gel (eluent: CH$_2$Cl$_2$/CH$_3$OH 95/5). The pure fractions were collected and the solvent evaporated. The residue was suspended in DIPE, filtered and dried. The solvent was evaporated and the residue was dried, yielding 3.25 g (59.3%) of (±)-1-[3,5-bis(trifluoromethyl)benzoyl]-2-[(3,4-dimethoxyphenyl)methyl]-4-piperidinone (interm. 16; mp. 132.7° C.).

In a similar way were prepared (±)-1-[3,5-bis(trifluoromethyl)benzoyl]-2-(imidazo[1,2-a]pyridin-3-yl)-4-piperidinone (interm. 17)

(±)-cis-1-(3,5-dimethylbenzoyl)-2-(phenylmethyl)-4-piperidinol (interm. 18; mp. 178.1° C.);

(±)-1-[3,5-bis(trifluoromethyl)benzoyl]-2-phenyl-4-piperidinone (interm. 19; mp. 119.4° C.);

(±)-trans-1-(3,5-dimethylbenzoyl)-2-(phenylmethyl)-4-piperidinol (interm. 20; mp. 153.2° C.).

EXAMPLE A8

Triethyl amine (7 ml) and methanesulfonyl chloride (3.4 ml) were added to a mixture of intermediate (18) (13 g) in CH$_2$Cl$_2$ (200 ml) and the mixture was stirred at RT for 3 hours. The mixture was washed with water, NaOH 50% and again with water. The organic layer was dried, filtered and the solvent evaporated. The residue was purified by column chromatography over silica gel (eluent: CH$_2$Cl$_2$/CH$_3$OH 99/1). The pure fractions were collected and the solvent evaporated, yielding 14.4 g (90%) of (±)-cis-1-(3,5-dimethylbenzoyl)-2-(phenylmethyl)-4-piperidinol methanesulfonate(ester) (interm. 21).

EXAMPLE A9 a) A mixture of (±)-ethyl 4-oxo-2-(phenylmethyl)-1-piperidinecarboxylate (10 g) and benzylamine (4 g) was hydrogenated at 50° C. in thiophene (4% solution; 1 ml) and methanol (150 ml) with palladium on activated carbon (10%; 3 g) as a catalyst. After uptake of hydrogen, the catalyst was filtered off and the solvent was evaporated, yielding (±)-ethyl 2-(phenylmethyl)-4-[(phenylmethyl)amino]-1-piperidine-carboxylate (interm. 22).

b) A mixture of intermediate (22) (12 g) was hydrogenated at 50° C. in methanol (150 ml) with palladium on activated carbon (10%; 2 g) as a catalyst. After uptake of hydrogen, the catalyst was filtered off and the solvent was evaporated. The residue was purified by column chromatography over silica gel (eluent: CH$_2$Cl$_2$/(CH$_3$OH/NH$_3$) 97/3 to 95/5). The pure fractions were collected and the solvent evaporated, yielding 6 g (67%) of (±)-ethyl 4-amino-2-(phenylmethyl)-1-piperidinecarboxylate (interm. 23).

c) Intermediate (23) (15.1 g), 2-chloro-1-(2-ethoxyethyl)-1H-benzimidazol (13.5 g) and copper (3.84 g) were stirred at 150° C. for 4 hours. The mixture was taken up in CH$_2$Cl$_2$ and filtered. The filtrate was washed with a NH$_4$OH solution and with water. The organic layer was dried, filtered and the solvent evaporated. The residue was purified by column chromatography over silica gel (eluent: CH$_2$Cl$_2$/CH$_3$OH 97/3). The pure fractions were collected and the solvent evaporated, yielding 20 g (77%) of (±)-ethyl cis-4-[[1-(2-ethoxyethyl)-1H-benzimidazol-2-yl]amino]-2-(phenylmethyl)-1-piperidinecarboxylate (interm. 24).

EXAMPLE A10

1-(2-ethoxyethyl)-1H-benzimidazol-2-amine (8.2 g) was added to (±)-ethyl 2-[(3,4-dichlorophenyl)methyl]-4-oxo-1-piperidinecarboxylate (13.2 g) in CH$_2$Cl$_2$ (20 ml). Titanium (IV)isopropoxide (13.64 g) was added and the mixture was stirred for 3 hours at RT. Sodiumborohydride (1.82 g) in ethanol (20 ml) was added and the reaction mixture was stirred overnight at RT. Water (20 ml) was added and the mixture was stirred for 5 minutes. CH$_2$Cl$_2$ (200 ml) was added and the mixture was stirred, dried, filtered, and the filtrate was evaporated. The residue was purified by column chromatography over silica gel (eluent: CH$_2$Cl$_2$/CH$_3$OH 98/2, upgrading to 97/3). The desired fractions were collected and the solvent was evaporated, yielding 2.6 g of (±)-ethyl trans-2-[(3,4-dichlorophenyl)methyl]-4-[[1-(2-ethoxyethyl)-1H-benzimidazol-2-yl]amino]-1-piperidinecarboxylate (interm. 25), and 6.2 g of (±)-ethyl cis-2-[(3,4-dichlorophenyl)methyl]-4-[[1-(2-ethoxyethyl)-1H-benzimidazol-2-yl]amino]-1-piperidinecarboxylate (interm. 26).

EXAMPLE A11

(±)-1,1-dimethylethyl trans-4-hydroxy-2-(phenylmethyl)-1-piperidinecarboxylate (25.6 g) was dissolved in N,N-dimethylformamide (256 ml). Sodiumhydride (4.24 g) was added and the mixture was stirred at RT for 1.5 hours. 2-chloro-1-(2-ethoxyethyl)-1H-benzimidazol (24.8 g) was added and the mixture was stirred at 70° C. for 18 hours. The solvent was evaporated, the residue taken up in water and CH$_2$Cl$_2$ and the layers were separated. The organic layer was dried, filtered and the solvent evaporated, yielding 50 g (100%) of (±)-1,1-dimethylethyl trans-4-[[1-(2-ethoxyethyl)-1H-benzimidazol-2-yl]oxy]-2-(phenylmethyl)-1-piperidine-carboxylate (interm 27).

EXAMPLE A12

A mixture of (±)-ethyl trans-2-[(3,4-dichlorophenyl)methyl]-4-[[1-(2-ethoxyethyl)-1H-benzimidazol-2-yl]amino]-1-piperidinecarboxylate (2.5 g) and KOH (2.8 g) in 2-propanol (50 ml) was stirred and refluxed for 48 hours. The solvent was evaporated. The residue was partitioned between water and CH$_2$Cl$_2$. The organic layer was separated, dried, filtered and the solvent evaporated. The residue was purified by column chromatography over silica gel (eluent: $CH_2Cl_2/(CH_3OH/NH_3)$ 95/5, upgrading to 90/10). The pure fractions were collected and the solvent was evaporated, yielding 1.1 g (49.2%) of (±)-trans-N-[2-[(3,4-dichlorophenyl)methyl]-4-piperidinyl]-1-(2-ethoxyethyl)-1H-benzimidazol-2-amine (interm. 28).

In a similar way were prepared:

(i)-cis-N-[2- [(3,4-dichlorophenyl)methyl]-4-piperidinyl]-1-(2-ethoxyethyl)-1H-benzimidazol-2-amine dihydrochloride.monohydrate.2-propanolate(2:1) (interm. 29); and (±)-cis-1-(2-ethoxyethyl)-N-[2-(phenylmethyl)-4-piperidinyl]-1H-benzimidazol-2-amine ethanedioate(1:2) (interm. 30).

EXAMPLE A13

A mixture of (±)-cis-N-[1,2-bis(phenylmethyl)-4-piperidinyl]-1-methyl-1H-benzimidazol-2-amine (4.7 g) in methanol (200 ml) was hydrogenated with palladium on activated carbon (10%; 2 g) as a catalyst. After uptake of hydrogen, the catalyst was filtered off and the filtrate was evaporated. The residue was purified by column chromatography over silica gel (eluent: $CH_2Cl_2/CH_3OH$ 95/5). The pure fractions were collected and the solvent evaporated. The residue was suspended in DIPE, filtered and dried, yielding 0.6 g (17%) of (±)-cis-1-methyl-N-[2-(phenylmethyl)-4-piperidinyl]-1H-benzimidazol-2-amine (interm. 31; mp. 86.3° C.).

EXAMPLE A14

(±)-1,1-dimethylethyl trans-4-[[1-(2-ethoxyethyl)-1H-benzimidazol-2-yl]amino]-2-(phenylmethyl)-1-piperidinecarboxylate (6 g) was taken up in methanol (160 ml). HCl in 2-propanol (16 ml) was added and the mixture was stirred and refluxed for 1 hour. The solvent was evaporated, the residue was taken up in water, diluted NaOH and extracted with $CH_2Cl_2$. The organic layer was separated and purified on a glass filter over silica gel (eluent: $CH_2Cl_2/(CH_3OH/NH_3)$ 95/5). The pure fractions were collected and the solvent evaporated. The residue was crystallized from DIPE, yielding 3 g (63.4%) (±)-trans-1-(2-ethoxyethyl)-N-[2-(phenylmethyl)-4-piperidinyl]-1H-benzimidazol-2-amine (interm. 32).

In a similar way were prepared:

(±)-trans-1-(2-ethoxyethyl)-2-[[2-(phenylmethyl)-4-piperidinyl]oxy]-1H-benzimidazole (interm. 33);

(±)-trans-N-[2-(phenylmethyl)-4-piperidinyl]-1-(2-thienylmethyl)-1H-benzimidazol-2-amine (interm. 34);

(±)-trans-1-[(4-fluorophenyl)methyl]-N-[2-(phenylmethyl)-4-piperidinyl]-1H-benzimidazol-2-amine (interm. 35; mp. 127.2° C.);

(±)-trans-1-[(2-methoxyphenyl)methyl]-N-[2-(phenylmethyl)-4-piperidinyl]-1H-benzimidazol-2-amine (interm. 36);

(±)-trans-N-[2-(phenylmethyl)-4-piperidinyl]-1-methyl-1H-benzimidazol-2-amino (interm. 37);

(±)-trans-1-[(2-methyl-5-oxazolyl)methyl]-N-[2-(phenylmethyl)-4-piperidinyl]-1H-benzimidazol-2-amine (interm. 38);

(±)-trans-1-[(5-methyl-2-furanyl)methyl]-N-[2-(phenylmethyl)-4-piperidinyl]-1H-2-benzimidazol-2-amine (interm. 39).

B. PREPARATION OF THE COMPOUNDS OF FORMULA (I)

EXAMPLE B1

A mixture of intermediate (1) (6.44 g) and 1-(2-ethoxyethyl)-N-piperidin-4-yl-1H-benzimidazol-2-amine (4.33 g) in thiophene (4% solution; 2 ml) and toluene (450 ml) was hydrogenated with palladium on activated carbon (10%; 1 g) as a catalyst in autoclave at 125° C. and under a pressure of 50 kg overnight. After uptake of hydrogen, the catalyst was filtered off and the filtrate was evaporated. The residue was purified by column chromatography over silica gel (eluent: $CH_2Cl_2/(CH_3OH/NH_3)$ 98/2). Fraction 1 was collected and evaporated. The residue was crystallized from $CH_3CN$, the precipitate was filtered off and dried, yielding 2.14 g (20%) of (±)-cis-1-[1,3-bis-(trifluoromethyl)benzoyl]-4-[4-[[1-(2-ethoxyethyl)-1H-benzimidazol-2-yl]amino]-1-piperidinyl]-2-(phenylmethyl)piperidine (comp. 5; mp. 201.5° C.). Fraction 2 was collected and evaporated. The residue was stirred up in petrol ether, the precipitate was filtered off and dried, yielding 1.04 g (10%) of (±)-trans-1-[1,3-bis(trifluoromethyl)-benzoyl]-4-[4-[[1-(2-ethoxyethyl)-1H-benzimidazol-2-yl]amino]-1-piperidinyl]-2-(phenylmethyl)piperidine (comp. 6; mp. 174.5° C.).

EXAMPLE B2

Titanium(IV)isopropoxide (3.55 g) was added to a mixture of intermediate (7) (3.78 g) and intermediate (1) (2.74 g) in ethanol (10 ml) and the mixture was stirred at RT for 6 hours. Sodium cyanoborohydride (0.65 g) in ethanol (5 ml) was added and the mixture was stirred at RT overnight. Water (10 ml) was added, stirred for 15 minutes, $CH_2Cl_2$ (200 ml) and $MgSO_4$ were added and the mixture was stirred for 15 minutes. The mixture was filtered and the solvent evaporated. The residue was purified by column chromatography over silica gel (eluent: $CH_2Cl_2/CH_3OH$ 98/2). The pure fractions were collected and evaporated. The residues (fraction A and fraction B) were purified by HPLC (eluent: toluene/2-propanol 95/5). The pure fractions were collected and evaporated. The residues were suspended in petrol ether, filtered off and dried, yielding 0.55 g (7%) of 2α,4α-trans-1-[3,5-bis(trifluoromethyl)benzoyl]-4-[4-[[1-(2-ethoxyethyl)-1H-benzimidazol-2-yl]amino]-2-(phenylmethyl)-1-piperidinyl]-2-(phenylmethyl)piperidine (comp. 13; mp. 115.3° C.) and 0.74 g (9.3%) of 2α,4β-trans-1-[3,5-bis(trifluoromethyl)benzoyl]-4-[4-[[1-(2-ethoxyethyl)- 1H-benzimidazol-2-yl]amino]-2-(phenylmethyl)-1-piperidinyl]-2-(phenylmethyl)piperidine (comp. 14; mp. 105.9° C.).

EXAMPLE B3 a) 3,5-bis(trifluoromethyl)benzoyl chloride (1.52 g) was added, followed by triethylamine (1.4 ml) to intermediate (7) (1.9 g) dissolved in $CH_2Cl_2$ (100 ml) and the mixture was stirred overnight. The mixture was washed with water and the layers were separated. The organic layer was dried, filtered and the solvent evaporated. The residue was purified by column chromatography over silica gel (eluent: $CH_2Cl_2/(CH_3OH/NH_3)$ 98/2). The pure fractions were collected and the solvent evaporated. The residue was crystallized from DIPE, yielding 2.47 g (80%) of (±)-trans-1-[3,5-bis(trifluoromethyl)benzoyl]-4-[[1-(2-ethoxyethyl)-1H-benzimidazol-2-yl]amino]-2-(phenylmethyl)piperidine (comp. 85; mp. 177.8° C.).

b) Compound (85) (0.5 g) was separated in its optical isomers by column chromatography Chiracel AD over silica gel (eluent: hexane/C$_2$H$_5$OH 80120) (20 μm). The pure fractions were collected and the solvent was evaporated, yielding 0.21 g (42.4%) of (A-trans)-1-[3,5-bis (trifluoromethyl)benzoyl]-4-[[1-(2-ethoxyethyl)-1H-benzimidazol-2-yl]amino]-2-(phenylmethyl)piperidine (comp. 94;mp. 110.0° C.; [α]$_D^{20}$=−22.97° (conc.=1% in CH$_3$OH)) and 0.24 g (48.5%) of (B-trans)-1-[3,5-bis-(trifluoromethyl)benzoyl]-4-[[1-(2-ethoxyethyl)-1H-benzimidazol-2-yl]amino]-2-(phenylmethyl)piperidine (comp. 95; mp. 111.5° C.; [α]$_D^{20}$=+22.96° (conc.=1% in CH$_3$OH)).

EXAMPLE B4

3-methyl-2-benzofurancarboxylic acid (0.100 g) and 1-hydroxy-1H-benzotriazole (0.070 g) were added to (±)-trans-1-[(2-methyl-5-oxazolyl)methyl]-N-[1-[2-(phenylmethyl)-4-piperidinyl]-4-piperidinyl]-1H-benzimidazol-2-amine (0.100 g) in CH$_2$Cl$_2$ (5 ml). The mixture was stirred under N$_2$ atmosphere. A solution of triethylamine (0.5 ml) and 1-(3-dimethylaminopropyl)-3-ethylcarbodiimide hydrochloride (1:1) (0.080 g) in CH$_2$Cl$_2$ (10 ml) was added dropwise and the reaction mixture was stirred overnight at RT, under N$_2$. Then, the compound was isolated and purified by column chromatography (eluent gradient: (0.5% ammoniumacetate in H$_2$O)/CH$_3$OH/CH$_3$CN 70/15/15 upgrading over 0/50/50 to 0/0/100). The desired fractions were collected and the solvent was evaporated, yielding 0.060 g of (±)-trans-1-[(3-methyl-2-benzofuranyl)-carbonyl]-4-[4-[[1-[(2-methyl-5-oxazolyl)methyl]-1H-benzimidazol-2-yl]amino]-1-piperidinyl]-2-(phenylmethyl) piperidine.

EXAMPLE B5

A mixture of (±)-trans-N-[3,5-bis(trifluoromethyl) phenyl]-4-[4-[[1-[(2-methyl-5-oxazolyl)methyl]-1H-benzimidazol-2-yl]amino]-1-piperidinyl]-2-(phenylmethyl)-1-piperidinecarboxamide (0.100 g) and 3,5-bis(trifluoromethyl) benzeneisocyanato (10 drops) in CH$_2$Cl$_2$ (2 ml) was stirred overnight at RT. Then, the compound was isolated and purified by column chromatography (eluent gradient: (0.5% ammoniumacetate in H$_2$O)/ CH$_3$OH/CH$_3$CN 70/15/15 upgrading over 0/50/50 to 0/0/100). The desired fractions were collected and the solvent was evaporated, yielding 0.050 g (±)-trans-N-[3,5-bis (trifluoromethyl)phenyl]-4-[4-[[1-[(2-methyl-5-oxazolyl) methyl]-1H-benzimidazol-2-yl]amino]-1-piperidinyl]-2-(phenylmethyl)-1-piperidinecarboxamide (comp.52).

EXAMPLE B6

(±)-cis-1-(3,5-dimethylbenzoyl)-2-(phenylmethyl)-4-piperidinamine (1.2 g), 2-chloro-1-(2-thienylmethyl)-1H-benzimidazole (2.24 g) and copper (0.6 g) were stirred at 150° C. for 5 hours. The mixture was taken up in CH$_2$Cl$_2$ and filtered. The filtrate was washed with diluted NH$_4$OH and stirred. The organic layer was separated, dried, filtered and the solvent evaporated. The residue was purified by column chromatography over silica gel (eluent: CH$_2$Cl$_2$/ (CH$_3$OH/NH$_3$) 97/3). The pure fractions were collected and the solvent evaporated. The residue was crystallized from CH$_3$CN, yielding 1.87 g (35%) of (±)-cis-1-(3,5-dimethylbenzoyl)-2-(phenylmethyl)-N-[1-(2-thienylmethyl)-1H-benzimidazol-2-yl]-4-piperidinamine (comp. 76; mp. 201.4° C.).

EXAMPLE B7

A mixture of (±)-1-[3,5-bis(trifluoromethyl)benzoyl]-2-(phenylmethyl)-4-piperidinone (4.29 g), 3-(2-furanylmethyl)-3H-imidazo[4,5-b]pyridin-2-amine (2.14 g) and titanium(IV)isopropoxide (3.41 g) in CH$_2$Cl$_2$ (5 ml) was stirred at RT for 3 hours. A mixture of sodium cyanoborohydride (0.628 g) in ethanol (5 ml) was added. The mixture was stirred at RT overnight. Water (5 ml) and CH$_2$Cl$_2$ (300 ml) were added. The mixture was stirred for 15 minutes. The biphasic mixture was dried, filtered and the filtrate was evaporated. The residue was purified by HPLC (eluent: 0.5% NH$_4$OC(O)CH$_3$/CH$_3$CN 40/60). Two desired fractions were collected and their solvent was evaporated. Each residue was dried and ground, yielding 1.22 g (19.4%) of (±)-cis-1-[3,5-bis(trifluoromethyl)benzoyl]-4-[[3-(2-furanylmethyl)-3H-imidazo-[4,5-b]pyridin-2-yl]amino]-2-(phenylmethyl)piperidine (comp. 112; mp. 108.7° C.) and 0.14 g (2.2%) of (±)-trans-1-[3,5-bis(trifluoromethyl) benzoyl]-4-[[3-(2-furanylmethyl)-3H-imidazo[4,5-b] pyridin-2-yl]amino]-2-(phenylmethyl)piperidine (comp. 113; mp. 108.3° C.).

EXAMPLE B8

(±)-cis-1-(3,5-dimethylbenzoyl)-2-(phenylmethyl)-4-piperidinol (2.6 g) dissolved in N,N-dimethylformamide (100 ml) was stirred under N$_2$. Sodium hydride (60%) (0.36 g) was added and the mixture was stirred at 40° C. for 1 hour. 2-Chloro-1-[(4-fluorophenyl)-methyl]-1H-benzimidazole (2.6 g) was added and the mixture was stirred at 60° C. for 20 hours. The solvent was evaporated and the residue was taken up in water and CH$_2$Cl$_2$. The organic layer was separated, dried, filtered and the solvent evaporated. The residue was purified by column chromatography over silica gel (eluent: CH$_2$Cl$_2$/CH$_3$OH 97/3). The pure fractions were collected and the solvent was evaporated. The residue was crystallized from DIPE, yielding 2.85 g (65%) of (±)-cis-1-(3,5-dimethylbenzoyl)-4-[[1-[(4-fluorophenyl)methyl]-1H-benzimidazol-2-yl]oxy]-2-(phenylmethyl)piperidine (comp. 70; mp. 154.1° C.).

EXAMPLE B9

A mixture of 1-(2-ethoxyethyl)-1H-benzimidazole-2-thiol (4.44 g), intermediate (21) (6 g) and potassium carbonate (2.76 g) in ethanol (300 ml) was stirred and refluxed overnight. The solvent was evaporated, the residue was taken up in water and extracted with CH$_2$Cl$_2$. The organic layer was dried, filtered and the solvent evaporated. The residue was purified by HPLC (eluent: CH$_3$OH/(H$_2$O/ NH$_4$OC(O)CH$_3$ 0.5%) 75/25). The pure fractions were collected and their solvent evaporated. The residue was separated by column chromatography over silica gel (eluent: CH$_2$Cl$_2$/CH$_3$OH 98/2 to 96/4). The pure fractions were collected and their solvent evaporated. Residue 1 was dried and grinded, yielding 0.71 g of (±)cis-1-(3,5-dimethylbenzoyl)-4-[[1-(2-ethoxy-ethyl)-1H-benzimidazol-2-yl]thio]-2-(phenylmethyl)piperidine (comp. 105). Residue 2 was dried and grinded, yielding 1.72 g of (±)-trans-1-(3, 5-dimethylbenzoyl)-4-[[1-(2-ethoxyethyl)-1H-benzimidazol-2-yl]thio]-2-(phenylmethyl)piperidine (comp. 106; mp. 147.3° C.).

EXAMPLE B10

Sodium hydride (0.22 g) was added to a mixture of compound (85) (2.8 g) in N,N-di-methylformamide (100 ml) and stirred. The mixture was stirred at 60° C. for 45 minutes. Iodomethane (0.78 g) was added and the mixture was stirred at 70° C. overnight. The solvent was evaporated and taken up in CH$_2$Cl$_2$ and water. The organic layer was separated, dried, filtered and the solvent evaporated. The residue was purified on a glass filter over silica gel (eluent: $CH_2Cl_2$/$CH_3OH$ 97/3). The pure fractions were collected and their solvent evaporated. The residue was crystallized from DIPE, filtered and dried, yielding 1.19 g (42%) of (±)-trans-1-[3,5-bis(trifluoromethyl)benzoyl]-4-[[1-(2-ethoxyethyl)-1H-benzimidazol-2-yl]methylamino]-2-(phenylmethyl)piperidine (comp. 108; mp. 155.2° C.).

EXAMPLE B11

3-Chlorobenzenecarboperoxoic acid (0.173 g) was added to a mixture of compound (106) (0.5 g) in $CH_2Cl_2$ (10 ml) and the mixture was stirred for 2.5 hours at RT. The mixture was washed with diluted NaOH, dried and the solvent evaporated. The residue was crystallized from $CH_3CN$. The residue was purified by HPLC (eluent: $CH_2Cl_2$/$CH_3OH$ 98/2). The pure fractions were collected and their solvent evaporated. The residues were dried, yielding 0.11 g of (A-trans)-1-(3,5-dimethylbenzoyl)-4-[[1-(2-ethoxyethyl)-1H-benzimidazol-2-yl]sulfinyl]-2-(phenylmethyl)piperidine (comp. 109) and 0.33 g of (B-trans)-1-(3,5-dimethylbenzoyl)-4-[[1-(2-ethoxyethyl)-1H-benzimidazol-2-yl]sulfinyl]-2-(phenylmethyl)piperidine (comp. 110).

EXAMPLE B12

Isatoic anhydride (0.49 g) was added to a mixture of (±)-trans-1-(2-ethoxyethyl)-N-[2-(phenylmethyl)-4-piperidinyl]-1H-benzimidazol-2-amine (1.14 g) in $CH_2Cl_2$ (150 ml), the mixture was stirred for 3 hours and then refluxed for 3 hours. The solvent was evaporated, 2-propanol (100 ml) was added to the residue and the mixture was refluxed for 18 hours. Isatoic anhydride (0.2 g) was added again and the mixture was refluxed for 4 hours. The solvent was evaporated and the residue was purified by column chromatography over silica gel (eluent: $CH_2Cl_2$/$CH_3OH$ 95/5). The pure fractions were collected and evaporated. The residue was crystallized from DIPE, yielding 0.5 g (33.4%) of (±)-trans-1-[2-aminobenzoyl]-4-[[1-(2-ethoxyethyl)-1H-benzimidazol-2-yl]amino]-2-(phenylmethyl)piperidine (comp 123; mp. 197.4° C.).

The following tables list compounds that were prepared according to one of the above examples (Ex.).

TABLE 1

| Co. No. | Ex | p | R | A | Y | R⁴ | R⁶ | Physical Data (mp. in ° C.) |
|---|---|---|---|---|---|---|---|---|
| 1 | B1 | 1 | $CH_3$ | CH | NH | $CH_2$—$CH_2$—O—$CH_2$—$CH_3$ | H | (±)-cis/102.0 |
| 2 | B1 | 1 | $CH_3$ | CH | NH | $CH_2$—$CH_2$—O—$CH_2$—$CH_3$ | H | (±)-trans/98.8 |
| 3 | B1 | 1 | $CH_3$ | CH | NH | $H_2C$—(2-fluorophenyl) | H | (±)-cis/134.5 |
| 4 | B1 | 1 | $CH_3$ | CH | NH | $H_2C$—(2-fluorophenyl) | H | (±)-trans/120.3 |
| 5 | B1 | 1 | $CF_3$ | CH | NH | $CH_2$—$CH_2$—O—$CH_2$—$CH_3$ | H | (±)-cis/201.5 |
| 6 | B1 | 1 | $CF_3$ | CH | NH | $CH_2$—$CH_2$—O—$CH_2$—$CH_3$ | H | (±)-trans/174.5 |
| 7 | B2 | 1 | $CH_3$ | CH | NH | —$CH_2$-(thiophene) | H | (±)-cis/121.8 |
| 8 | B2 | 1 | $CH_3$ | CH | NH | —$CH_2$-(thiophene) | H | (±)-trans/139.6 |

TABLE 1-continued
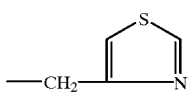
| Co. No. | Ex | p | R | A | Y | R⁴ | R⁶ | Physical Data (mp. in ° C.) |
|---|---|---|---|---|---|---|---|---|
| 9 | B2 | 1 | $CH_3$ | CH | NH | 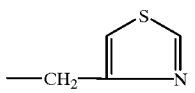 | H | (±)-cis/134.1 |
| 10 | B2 | 1 | $CH_3$ | CH | NH | 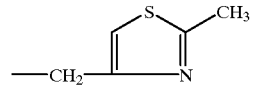 | H | (±)-trans/134.9 |
| 11 | B2 | 1 | $CH_3$ | CH | $CH_2$ | 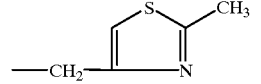 | H | (±)-cis/90.6 |
| 12 | B2 | 1 | $CH_3$ | CH | $CH_2$ | 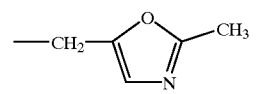 | H | (±)-trans/95.1 |
| 13 | B2 | 1 | $CF_3$ | CH | NH | $CH_2-CH_2-O-CH_2-CH_3$ | benzyl | 2α, 4α trans/ 115.3 |
| 14 | B2 | 1 | $CF_3$ | CH | NH | $(CH_2)_2-O-CH_2-CH_3$ | benzyl | 2α, 4β trans/ 105.9 |
| 15 | B2 | 1 | $CF_3$ | CH | NH | 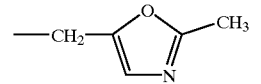 | H | (±)-cis/149.0 |
| 16 | B2 | 1 | $CF_3$ | CH | NH | 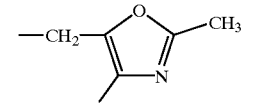 | H | (±)-trans |
| 17 | B2 | 1 | $CF_3$ | N | NH | 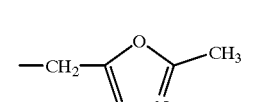 | H | (±)-cis/123.5 |
| 18 | B2 | 1 | $CF_3$ | N | NH | 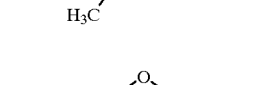 | H | (±)-trans/153.8 |
| 19 | B2 | 1 | $CF_3$ | N | NH | (furan with CH₃) | H | (±)-cis/148.1 |

TABLE 1-continued

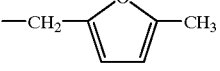

| Co. No. | Ex | p | R | A | Y | R⁴ | R⁶ | Physical Data (mp. in ° C.) |
|---|---|---|---|---|---|---|---|---|
| 20 | B2 | 1 | CF₃ | N | NH | —CH₂-(5-methyl-2-furyl) | H | (±)-trans/107.6 |
| 21 | B2 | 1 | CF₃ | CH | CHOH | —CH₂-(5-methyl-2-furyl) | H | A-cis/110.2 |
| 22 | B2 | 1 | CF₃ | CH | CHOH | —CH₂-(5-methyl-2-furyl) | H | B-cis/108.7 |
| 23 | B2 | 1 | CF₃ | CH | CHOH | —CH₂-(5-methyl-2-furyl) | H | (±)-trans/185.5 |
| 24 | B2 | 1 | CF₃ | CH | O | —CH₂-(4-fluorophenyl) | H | (±)-cis/130.9 |
| 25 | B2 | 1 | CF₃ | CH | O | —CH₂-(4-fluorophenyl) | H | (±)-trans/168.8 |
| 26 | B2 | 1 | CF₃ | CH | NH | —CH₂-(4-fluorophenyl) | H | (±)-cis/220.6 |
| 27 | B2 | 1 | CF₃ | CH | NH | —CH₂-(4-fluorophenyl) | H | (±)-trans/126.4 |
| 28 | B2 | 1 | CF₃ | CH | NH | —CH₂-(5-methyl-2-furyl) | H | (±)-cis/181.8 |
| 29 | B2 | 1 | CF₃ | CH | NH | —CH₂-(5-methyl-2-furyl) | H | (±)-trans/130.0/ hydrate(1:1) |
| 30 | B2 | 0 | CF₃ | N | NH | —CH₂-(5-methyl-2-furyl) | H | (±)-cis/90.8 |

TABLE 1-continued

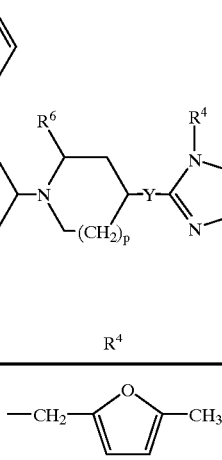

| Co. No. | Ex | p | R | A | Y | R⁴ | R⁶ | Physical Data (mp. in ° C.) |
|---|---|---|---|---|---|---|---|---|
| 31 | B2 | 0 | CF₃ | N | NH | —CH₂-(5-methyl-2-furyl) | H | (±)-trans/80.7/ hydrate (1:1) |
| 32 | B3a | 1 | CH₃ | CH | NH | —CH₂-(5-methyl-2-furyl) | H | (±)-trans |
| 33 | B2b | 1 | CF₃ | CH | CH₂ | —CH₂-(4-fluorophenyl) | H | (±)-trans |
| 34 | B2a | 1 | CF₃ | CH | S | —CH₂-(4-fluorophenyl) | H | (+)-cis |
| 35 | B2a | 1 | CF₃ | CH | S | —CH₂-(4-fluorophenyl) | H | (±)-trans |
| 36 | B2a | 1 | CF₃ | CH | O | —CH₂-(2-methyl-5-oxazolyl) | H | (±)-cis |
| 37 | B2a | 1 | CF₃ | CH | O | —CH₂-(2-methyl-5-oxazolyl) | H | (±)-trans |
| 38 | B3a | 1 | H | CH | NH | —CH₂-(2-methyl-5-oxazolyl) | H | (+)-trans |
| 40 | B2b | 1 | CF₃ | CH | CH₂ | —CH₂-(4-fluorophenyl) | H | (±)-czs |
| 41 | B2a | 1 | CF₃ | CH | CH₂ | —CH₂-(5-methyl-2-furyl) | H | (±)-trans |
| 42 | B2a | 1 | CF₃ | CH | CH₂ | —CH₂-(5-methyl-2-furyl) | H | (±)-cis |

TABLE 1-continued

| Co. No. | Ex | p | R | A | Y | R⁴ | R⁶ | Physical Data (mp. in ° C.) |
|---|---|---|---|---|---|---|---|---|
| 43 | B2a | 1 | CF₃ | CH | NH | —CH₂—(2-furanyl)—CH₂—OH | H | (±)-trans |
| 44 | B2a | 1 | CF₃ | CH | NH | —CH₂—(2-furanyl)—CH₂—OH | H | (±)-cis |

TABLE 2

| Co. No. | Ex | X | R² | R | Physical Data (mp. in ° C.) |
|---|---|---|---|---|---|
| 45 | B3a | direct bond | 2-naphalenyl | direct bond | (±)-trans |
| 46 | B3a | direct bond | 2-furanyl | direct bond | (±)-trans |
| 47 | B3a | direct bond | phenyl | direct bond | (±)-trans |
| 48 | B3a | direct bond | α-methylbenzyl (PhCH(CH₃)—) | direct bond | (±)-trans |
| 49 | B3a | NH | 3,5-bis-trifluoromethyl)phenyl | direct bond | (±)-trans |
| 50 | B4 | direct bond | 6-benzothiazolyl | direct bond | (±)-trans |
| 51 | B4 | direct bond | 5-fluoro-2-indolyl | direct bond | (±)-trans |
| 52 | B5 | NH | 3,5-bis(trifluoromethyl)phenyl | 4-piperidinyl | (±)-trans |
| 53 | B3a | direct bond | 3-cyanophenyl | 4-piperidinyl | (±)-trans |
| 54 | B3a | direct bond | 3-(1-methylethoxy)phenyl | 4-piperidinyl | (+)-trans |
| 55 | B3a | direct bond | 3,5-dichlorophenyl | 4-piperidinyl | (±)-trans |
| 56 | B3a | direct bond | 2-thienyl | 4-piperidinyl | (±)-trans |
| 57 | B3a | direct bond | 2-quinolinyl | 4-piperidinyl | (±)-trans |
| 58 | B3a | direct bond | 3,4,5-trimethoxyphenyl | 4-piperidinyl | (±)-cis |
| 59 | B3a | direct bond | 2-thienyl | 4-piperidinyl | (±)-cis |
| 60 | B3a | direct bond | 5-methyl-3-isoxazolyl | 4-piperidinyl | (±)-cis |
| 61 | B3a | direct bond | 2,6-dichloropyridinyl | 4-piperidinyl | (±)-cis |
| 62 | B3a | direct bond | 2-quinoxalinyl | 4-piperidinyl | (±)-cis |
| 63 | B3a | direct bond | 3-(1-methylethoxy)phenylmethyl | 4-piperidinyl | (±)-cis |
| 64 | B3a | S | phenyl | 4-piperidinyl | (±)-cis |

TABLE 2-continued

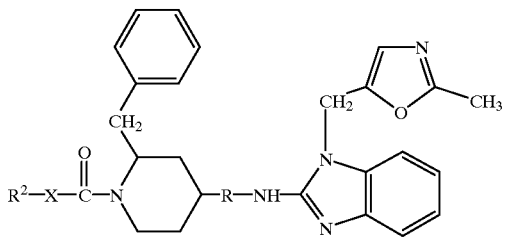

| Co. No. | Ex | X | R² | R | Physical Data (mp. in ° C.) |
|---|---|---|---|---|---|
| 65 | B4 | direct bond | 2,4-dimethyl-5-thiazolyl | 4-piperidinyl | (±)-cis |
| 66 | B4 | direct bond | 5-methyl-2-pyrazinyl | 4-piperidinyl | (±)-trans |
| 67 | B4 | direct bond | 3-methyl-2-benzofuranyl | 4-piperidinyl | (±)-trans |
| 68 | B4 | direct bond | 5-fluoro-2-indolyl | 4-piperidinyl | (±)-trans |

TABLE 3

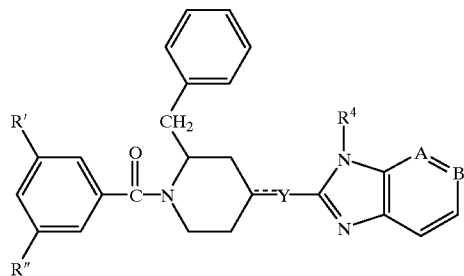

| Co. No. | Ex. No. | R' | R" | ----Y---- | R⁴ | —A=B— | Physical data (mp. in ° C. |
|---|---|---|---|---|---|---|---|
| 69 | B8 | —CH₃ | —CH₃ | —O— | —CH₃ | —CH=CH— | 171.1; (±)-cis |
| 70 | B8 | —CH₃ | —CH₃ | —O— | (4-fluorophenyl)methyl | —CH=CH— | 154.1; (±)-cis |
| 71 | B8 | —CH₃ | —CH₃ | —O— | (2-methoxyphenyl)methyl | —CH=CH— | 151.7; (±)-cis |
| 72 | B8 | —CH₃ | —CH₃ | —O— | —CH₃ | —CH=CH— | 185.6; (±)-trans |
| 73 | B3a | —CH₃ | —CH₃ | —NH— | —CH₃ | —CH=CH— | 185.9; (±)-cis |
| 74 | B3a | —CH₃ | —CH₃ | —NH— | —(CH₂)₂—O—CH₂—CH₃ | —CH=CH— | 166.4; (±)-trans |
| 75 | B3a | —CH₃ | —CH₃ | —NH— | —(CH₂)₂—O—CH₂—CH₃ | —CH=CH— | 123.9; (±)-cis |
| 76 | B6 | —CH₃ | —CH₃ | —NH— | 2-thienylmethyl | —CH=CH— | 201.4; (±)-cis |
| 77 | B3a | —CH₃ | —CH₃ | —NH— | (4-fluorophenyl)methyl | —CH=CH— | 249.9; (±)-trans |
| 78 | B3a | —CH₃ | —CH₃ | —NH— | 2-thienylmethyl | —CH=CH— | 250.7; (±)-trans |
| 79 | B3a | —CH₃ | —CH₃ | —NH— | (2-methoxyphenyl)methyl | —CH=CH— | 154.1; (±)-trans |
| 80 | B8 | —CH₃ | —CH₃ | —O— | —(CH₂)₂—O—CH₂—CH₃ | —CH=CH— | 67.2; (±)-cis |
| 81 | B8 | —CH₃ | —CH₃ | —O— | 2-thienylmethyl | —CH=CH— | 196.0; (±)-trans |
| 82 | B8 | —CH₃ | —CH₃ | —O— | —(CH₂)₂—O—CH₂—CH₃ | —CH=CH— | 55.9; (±)-trans |
| 83 | B3a | —CH₃ | —CH₃ | —NH— | —CH₃ | —CH=CH— | 51.7; (±)-trans; H₂O |
| 84 | B3a | —CH₃ | —CH₃ | —NH— | (2-methyl-5-oxazolyl)-methyl | —CH=CH— | 226.3; (±)-trans |
| 85 | B3a | —CF₃ | —CF₃ | —NH— | —(CH₂)₂—O—CH₂—CH₃ | —CH=CH— | 177.8; (±)-trans |
| 86 | B3a | —H | —H | —NH— | —(CH₂)₂—O—CH₂—CH₃ | —CH=CH— | (±)-trans |
| 87 | B3a | —H | —CH₃ | —NH— | —(CH₂)₂—O—CH₂—CH₃ | —CH=CH— | (±)-trans |
| 88 | B3a | —H | —CN | —NH— | —(CH₂)₂—O—CH₂—CH₃ | —CH=CH— | (±)-trans |
| 89 | B3a | —H | —CF₃ | —NH— | —(CH₂)₂—O—CH₂—CH₃ | —CH=CH— | (±)-trans |
| 90 | B3a | —OCH₃ | —OCH₃ | —NH— | —(CH₂)₂—O—CH₂—CH₃ | —CH=CH— | (±)-trans |
| 91 | B3a | —Cl | —Cl | —NH— | —(CH₂)₂—O—CH₂—CH₃ | —CH=CH— | (±)-trans |
| 92 | B3a | —F | —F | —NH— | —(CH₂)₂—O—CH₂—CH₃ | —CH=CH— | 173.7; (±)-trans |
| 93 | B8 | —CH₃ | —CH₃ | —O— | (2-methyl-5-oxazolyl)-methyl | —CH=CH— | 155.1; (±)-trans |
| 94 | B3b | —CF₃ | —CF₃ | —NH— | —(CH₂)₂—O—CH₂—CH₃ | —CH=CH— | 110.0; $[\alpha]_D^{20}$ = −22.97 (conc. = 1% in CH₃OH); A-trans; |
| 95 | B3b | —CF₃ | —CF₃ | —NH— | —(CH₂)₂—O—CH₂—CH₃ | —CH=CH— | 111.5; $[\alpha]_D^{20}$ = |

TABLE 3-continued

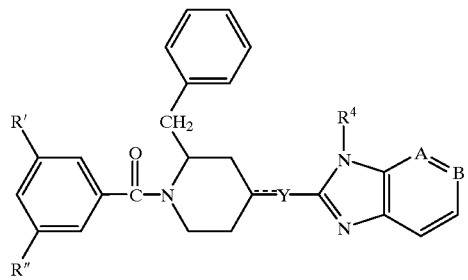

| Co. No. | Ex. No. | R' | R" | ---Y--- | R⁴ | —A=B— | Physical data (mp. in ° C. |
|---|---|---|---|---|---|---|---|
| | | | | | | | +22.96 (conc. = 1% in CH₃OH); B-trans |
| 96 | B3a | —CF₃ | —CF₃ | —O— | —(CH₂)₂—O—CH₂—CH₃ | —CH=CH— | 115.9; (±)-trans |
| 97 | B3 | —CF₃ | —CF₃ | —NH— | —(CH₂)₂—O—CH₂—CH₃ | —CH=CH— | 77.5; [α]$_D^{20}$ = -5.99° (conc. = 1% in CH₃OH); B-cis |
| 98 | B3a | —CF₃ | —CF₃ | —NH— | (2-methyl-5-furanyl)methyl | —CH=CH— | 204.8; (±)-trans |
| 99 | B3a | —CF₃ | —CF₃ | —NH— | (2-methyl-5-furanyl)methyl | —CH=CH— | 211.0; (±)-trans |
| 100 | B3a | —CH₃ | —CH₃ | —NH— | (2-methyl-5-furanyl)methyl | —CH=CH— | 188.0; (±)-trans |
| 101 | B3a | —OCH₃ | —OCH₃ | —O— | —(CH₂)₂—O—CH₂—CH₃ | —CH=CH— | (±)-trans |
| 102 | B3a | —Cl | —Cl | —O— | —(CH₂)₂—O—CH₂—CH₃ | —CH=CH— | (±)-trans |
| 103 | B3a | —H | —CF₃ | —O— | —(CH₂)₂—O—CH₂—CH₃ | —CH=CH— | (±)-trans |
| 104 | B3a | —F | —F | —O— | —(CH₂)₂—O—CH₂—CH₃ | —CH=CH— | (±)-trans |
| 105 | B9 | —CH₃ | —CH₃ | —S— | —(CH₂)₂—O—CH₂—CH₃ | —CH=CH— | (±)-cis |
| 106 | B9 | —CH₃ | —CH₃ | —S— | —(CH₂)₂—O—CH₂—CH₃ | —CH=CH— | 147.3; (±)-trans |
| 107 | B3 | —CF₃ | —CF₃ | —NH— | —(CH₂)₂—O—CH₂—CH₃ | —CH=CH— | 80.4; A-cis |
| 108 | B10 | —CF₃ | —CF₃ | —N—CH₃— | —(CH₂)₂—O—CH₂—CH₃ | —CH=CH— | 115.2; (±)-trans |
| 109 | B11 | —CH₃ | —CH₃ | —SO— | —(CH₂)₂—O—CH₂—CH₃ | —CH=CH— | A-trans |
| 110 | B11 | —CH₃ | —CH₃ | —SO— | —(CH₂)₂—O—CH₂—CH₃ | —CH=CH— | B-trans |
| 111 | B3a | —CF₃ | —F | —NH— | —(CH₂)₂—O—CH₂—CH₃ | —CH=CH— | (±)-trans |
| 112 | B7 | —CF₃ | —CF₃ | —NH— | 2-furanylmethyl | —N=CH— | 108.7; (±)-cis |
| 113 | B7 | —CF₃ | —CF₃ | —NH— | 2-furanylmethyl | —N=CH— | 108.3; (±)-trans |
| 114 | B3 | —CF₃ | —CF₃ | —NH— | (2-methyl-5-oxazolyl)methyl | —CH=CH— | 108.2, [α]$_D^{20}$ = +24.77° (conc. = in CH₃OH); A-trans |
| 115 | B3 | —CF₃ | CF₃ | —NH— | (2-methyl-5-oxazolyl)methyl | —CH=CH— | 110–120, [α]$_D^{20}$ = -25.07° (conc. = 1% in CH₃OH); B-trans |

TABLE 4

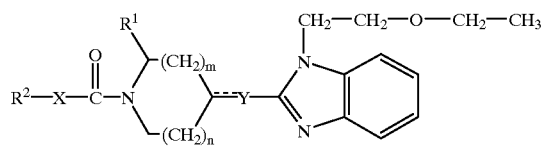

| Co. No. | Ex. | m | n | X$^\&$ | ---Y--- | R¹ | R² | Physical Data (mp. in ° C.) |
|---|---|---|---|---|---|---|---|---|
| 116 | 13a | 1 | 1 | d.b. | —NH— | phenylmethyl | 2,4-dichlorophenyl | (±)-trans |
| 117 | 13a | 1 | 1 | d.b. | —NH— | phenylmethyl | 4-chlorophenylmethyl | (±)-trans |
| 118 | 13a | 1 | 1 | d.b. | —NH— | phenylmethyl | 2-naphtalenyl | (±)-trans |
| 119 | 13a | 1 | 1 | d.b. | —NH— | phenylmethyl | 2-naphtalenylmethyl | (±)-trans |
| 120 | 13a | 1 | 1 | —O— | —NH— | phenylmethyl | phenylmethyl | (±)-trans |
| 121 | 13a | 1 | 1 | d.b. | —NH— | phenylmethyl | 1-phenylethyl | (±)-trans; mp. 74.9 |
| 122 | 13a | 1 | 1 | d.b. | —NH— | phenylmethyl | 1-methyl-2-pyrrolyl | (±)-trans; mp. 117.6 |
| 123 | 20 | 1 | 1 | d.b. | —NH— | phenylmethyl | 2-aminophenyl | (±)-trans; mp. 197.4 |

TABLE 4-continued $$R^2-X-\overset{O}{\underset{}{C}}-N\underset{(CH_2)_n}{\overset{(CH_2)_m}{\diagup}}Y\text{-benzimidazole with }N-CH_2-CH_2-O-CH_2-CH_3$$

| Co. No. | Ex. | m | n | X[&] | ----Y---- | R¹ | R² | Physical Data (mp. in ° C.) |
|---|---|---|---|---|---|---|---|---|
| 124 | 13a | 1 | 1 | d.b. | —NH— | phenylmethyl | 3-(2-propoxy)-phenylmethyl | (±)-trans; mp. 55.3 |
| 125 | 13a | 1 | 1 | d.b. | —O— | phenylmethyl | 3,4-dichlorophenyl | (±)-trans |
| 126 | 13a | 1 | 1 | d.b. | —O— | phenylmethyl | 2-naphtalenyl | (±)-trans |
| 127 | 13a | 1 | 1 | d.b. | —O— | phenylmethyl | 1-phenylethyl | (±)-trans |
| 128 | 13a | 1 | 1 | d.b. | —O— | phenylmethyl | 4-chlorophenylmethyl | (±)-trans |
| 129 | 13a | 1 | 1 | d.b. | —O— | phenylmethyl | 2-quinolinyl | (±)-trans |
| 130 | 13a | 1 | 1 | d.b. | —O— | phenylmethyl | 2-naphtalenylmethyl | (±)-trans |
| 131 | 15 | 1 | 1 | d.b. | —NH— | phenyl | 3,5-bis(trifluoro)phenyl | (±)-cis; mp. 84.9 |
| 132 | 13a | 1 | 1 | d.b. | —NH— | phenylmethyl | 2,4-bis(trifluoro)phenyl | (±)-trans |
| 133 | 13a | 1 | 1 | d.b. | —NH— | phenylmethyl | 2-trifluorophenyl | (±)-trans |
| 134 | 13a | 1 | 1 | d.b. | —NH— | phenylmethyl | 2-trifluoro-4-fluorophenyl | (±)-trans |
| 135 | 13a | 1 | 1 | d.b. | —NH— | phenylmethyl | 2,5-bis(trifluoro)phenyl | (±)-trans |
| 136 | 13a | 1 | 1 | d.b. | —NH— | phenylmethyl | 2-fluoro-6-trifluorophenyl | (±)-trans |
| 137 | 13a | 1 | 1 | d.b. | —NH— | phenylmethyl | 2-fluoro-3-trifluorophenyl | (±)-trans |
| 138 | 13a | 1 | 1 | d.b. | —NH— | phenylmethyl | 3-trifluoro-4-fluorophenyl | (±)-trans |
| 139 | 13a | 1 | 1 | d.b. | —NH— | phenylmethyl | 2-fluoro-5-trifluorophenyl | (±)-trans |
| 140 | 13a | 1 | 1 | d.b. | —NH— | (3,4-dichlorophenyl)methyl | 3,5-bis(trifluoro)phenyl | (±)-cis; mp. 88.3 |
| 141 | 13a | 1 | 1 | d.b. | —NH— | (3,4-dichlorophenyl)methyl | 3,5-bis(trifluoro)phenyl | (±)-trans; mp. 194.9 |
| 142 | 15 | 1 | 1 | d.b. | —NH— | (3,4-dimethoxyphenyl)methyl | 3,5-bis(trifluoro)phenyl | (±)-trans |
| 143 | 13a | 1 | 1 | d.b. | —NH— | phenylmethyl | 2,6-bis(trifluoro)phenyl | (±)-trans; mp. 212.1 |
| 144 | B3a | 1 | 1 | d.b. | —NH— | 4-chlorophenyl-methyl | 2,5-bis(trifluoro)phenyl | (±)-trans |
| 145 | B3a | 1 | 1 | d.b. | —NH— | 4-chlorophenyl-methyl | 2,5-bis(trifluoro)phenyl | (±)-cis |
| 146 | B2a | 1 | 1 | d.b. | —NH— | 4-(trifluoro)-phenylmethyl | 3,5-bis(trifluoro)phenyl | (±)-cis |
| 147 | B2b | 1 | 1 | d.b. | NH | 3,4-difluoro-phenylmethyl | 3,5-bis(trifluoro)phenyl | (±)-trans |
| 148 | B2b | 1 | 1 | d.b. | NH | 3,4-difluoro-phenylmethyl | 3,5-bis(trifluoro)phenyl | (±)-cis |
| 149 | B2a | 1 | 2 | d.b. | NH | phenylmethyl | 3,5-bis(trifluoro)phenyl | (±)-(cis + trans) |
| 150 | B2a | 2 | 1 | d.b. | NH | phenylmethyl | 3,5-bis(trifluoro)phenyl | (±)-(cis + trans) |

[&]d.b. means direct bond

C. PHARMACOLOGICAL EXAMPLES

EXAMPLE C1

Antagonism of substance P induced relaxation of the pig coronary arteries

Segments of coronary arteries taken from pigs (killed by injection of an overdose of sodium pentobarbital) were inverted and mounted for recording of isometric tension in organ baths (volume 20 ml) with the endothelium at the outside. The preparations were bathed in Krebs - Henseleit solution. The solution was kept at 37° C. and gassed with a mixture of $O_2/CO_2$ (95/5). After stabilisation of the preparations, prostaglandin $F_{2\alpha}$ ($10^{-5}$M) was administered to induce a contraction. This was repeated until contractile responses became stable. Then prostaglandin $F_{2\alpha}$ was again administered and substance P ($3\times 10^{-10}$M and $10^{-9}$M cumulatively) was added. Substance P induced endothelium dependent relaxations. After washing away the agonists, a known concentration of a compound of formula (I) was added. After an incubation period of 30 minutes, prostaglandin $F_{2\alpha}$($10^{-5}$M) and the same concentrations of substance P as described above were again administered in the presence of the compound to be tested. Relaxations caused by substance P were expressed as relaxations under control conditions, and the percentage inhibition (% inhibition) of the response to $10^{-9}$M substance P was taken as a measure of the antagonistic activity of the compound to be tested. The results for the compounds of the present invention at a certain test concentration are listed in table 5.

TABLE 5

| Comp. No. | Concentration test compound | % inhibition | Comp. No. | Concentration test compound | % inhibition |
|---|---|---|---|---|---|
| 1 | $3 \times 10^{-8}$ | 15.0 | 29 | $3 \times 10^{-8}$ | 65.6 |
| 2 | $3 \times 10^{-8}$ | 41.1 | 30 | $3 \times 10^{-8}$ | 87.5 |
| 3 | $3 \times 10^{-7}$ | 35.2 | 31 | $3 \times 10^{-9}$ | 90.6 |
| 4 | $3 \times 10^{-8}$ | 10.2 | 44 | $3 \times 10^{-8}$ | 91.5 |

TABLE 5-continued

| Comp. No. | Concentration test compound | % inhibition | Comp. No. | Concentration test compound | % inhibition |
|---|---|---|---|---|---|
| 5 | $3 \times 10^{-8}$ | 80.7 | 43 | $3 \times 10^{-8}$ | 85.2 |
| 6 | $3 \times 10^{-8}$ | 85.3 | 150 | $3 \times 10^{-8}$ | 98.1 |
| 7 | $3 \times 10^{-8}$ | 54.0 | 149 | $3 \times 10^{-8}$ | 12.7 |
| 8 | $1 \times 10^{-8}$ | 14.7 | 42 | $3 \times 10^{-8}$ | 96.9 |
| 9 | $3 \times 10^{-8}$ | 78.1 | 41 | $3 \times 10^{-9}$ | 82.6 |
| 10 | $3 \times 10^{-8}$ | 89.3 | 36 | $3 \times 10^{-9}$ | 66 |
| 11 | $3 \times 10^{-8}$ | 81.1 | 145 | $3 \times 10^{-9}$ | 92.2 |
| 12 | $3 \times 10^{-8}$ | 92.3 | 40 | $3 \times 10^{-8}$ | 93.3 |
| 13 | $3 \times 10^{-8}$ | 19.9 | 33 | $3 \times 10^{-9}$ | 56.8 |
| 14 | $3 \times 10^{-8}$ | 53.3 | 144 | $3 \times 10^{-9}$ | 88.4 |
| 15 | $3 \times 10^{-8}$ | 84.6 | 147 | $3 \times 10^{-8}$ | 95.6 |
| 16 | $3 \times 10^{-8}$ | 88.8 | 148 | $3 \times 10^{-8}$ | 100 |
| 17 | $3 \times 10^{-8}$ | 94.5 | 34 | $3 \times 10^{-8}$ | 69.6 |
| 18 | $3 \times 10^{-9}$ | 73.7 | 35 | $3 \times 10^{-8}$ | 88.5 |
| 19 | $3 \times 10^{-9}$ | 79.5 | 146 | $3 \times 10^{-9}$ | 51.8 |
| 20 | $3 \times 10^{-9}$ | 68.9 | 37 | $3 \times 10^{-9}$ | 70.5 |
| 21 | $3 \times 10^{-8}$ | 95.8 | 32 | $3 \times 10^{-9}$ | 20.1 |
| 22 | $3 \times 10^{-9}$ | 89.4 | 54 | $3 \times 10^{-9}$ | 7.3 |
| 23 | $3 \times 10^{-9}$ | 94.3 | 55 | $3 \times 10^{-9}$ | 28.1 |
| 24 | $3 \times 10^{-8}$ | 100 | 56 | $3 \times 10^{-9}$ | 8.7 |
| 25 | $3 \times 10^{-8}$ | 100 | 65 | $3 \times 10^{-9}$ | 9.7 |
| 26 | $3 \times 10^{-8}$ | 82.2 | 52 | $3 \times 10^{-9}$ | 6.3 |
| 27 | $3 \times 10^{-8}$ | 92.8 | 46 | $3 \times 10^{-9}$ | 17.6 |
| 28 | $3 \times 10^{-8}$ | 100 | 45 | $3 \times 10^{-9}$ | 13.1 |

D. COMPOSITION EXAMPLES

"Active ingredient" (A.I.) as used throughout these examples relates to a compound of formula (I) a pharmaceutically acceptable addition salt, a stereochemically isomeric form thereof or a N-oxide form thereof.

EXAMPLE D.1: ORAL SOLUTION

Methyl 4-hydroxybenzoate (9 g) and propyl 4-hydroxybenzoate (I g) were dissolved in boiling purified water (4 l). In 3 l of this solution were dissolved first 2,3-dihydroxy-butanedioic acid (10 g) and thereafter A.I (20 g). The latter solution was combined with the remaining part of the former solution and 1,2,3-propanetriol (12 l) and sorbitol 70% solution (3 l) were added thereto. Sodium saccharin (40 g) were dissolved in water (500 ml) and raspberry (2 ml) and gooseberry essence (2 ml) were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.2: FILM-COATED TABLETS

Preparation of tablet core

A mixture of A.I. (100 g), lactose (570 g) and starch (200 g) was mixed well and thereafter humidified with a solution of sodium dodecyl sulfate (5 g) and polyvinyl-pyrrolidone (10 g) in water (200 ml). The wet powder mixture was sieved, dried and sieved again. Then there was added microcrystalline cellulose (100 g) and hydrogenated vegetable oil (15 g). The whole was mixed well and compressed into tablets, giving 10.000 tablets, each containing 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (25 ml). Polyethylene glycol (10 g) was molten and dissolved in $CH_2Cl_2$ (75 ml). The latter solution was added to the former and then there were added agnesium octadecanoate (2.5 g), polyvinylpyrrolidone (5 g) and concentrated colour suspension (30 ml) and the whole was homogenated. The tablet cores were coated with the thus obtained mixture in a coating apparatus.

EXAMPLE D.3: INJECTABLE SOLUTION

Methyl 4-hydroxybenzoate (1.8 g) and propyl 4-hydroxybenzoate (0.2 g) were dissolved in boiling water (500 ml) for injection. After cooling to about 50° C. there were added while stirring lactic acid (4 g), propylene glycol (0.05 g) and the A.I. (4 g). The solution was cooled to RT and supplemented with water for injection q.s. ad 1 l, giving a solution comprising 4 mg/ml of A.I. The solution was sterilized by filtration and filled in sterile containers.

What is claimed is:

1. A compound of formula

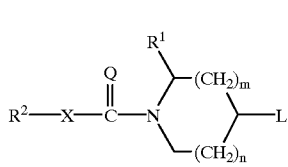

(I)

a N-oxide form, a pharmaceutically acceptable addition salt or a stereochemically isomeric form thereof, wherein n is 0, 1 or 2;

m is 1 or 2, provided that if m is 2, then n is 1;

X is a covalent bond or a bivalent radical of formula —O—, —S—OR, —$NR^3$—;

=Q is =O or =$NR^3$;

$R^1$ is $Ar^1$l, $Ar^1C_{1-6}$alkyl or di($Ar^1$)$C_{1-6}$alkyl wherein the $C_{1-6}$alkyl group is optionally substituted with hydroxy, $C_{1-4}$alkyloxy, oxo or a ketalized oxo substituent of formula —O—$CH_2$—$CH_2$—O— or —O—$CH_2$—$CH_2$—$CH_2$—O—;

$R^2$ is $Ar^2$, $Ar^2C_{1-6}$alkyl, Het or Het$C_{1-6}$alkyl;

L is a radical of formula

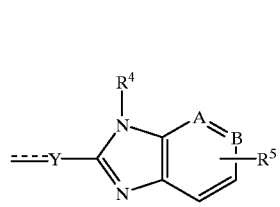

(A)

(B)

wherein p is 0, 1 or 2;

..... Y— is a bivalent radical of formula —$CH_2$—, —CH(OH)—, —C(=O)—, —O—, —S—, —S(=O)—, —S(=O)$_2$—, —$NR^3$—, —$CH_2$—$NR^3$— or —C(=O)—$NR^3$—; or a trivalent radical of formula =CH—;

—A=B— is a bivalent radical of formula —CH=CH—, —N=CH— or —CH=N—;

$R^3$ independently is hydrogen or $C_{1-6}$alkyl;
$R^4$ is hydrogen, $C_{1-6}$alkyl, $C_{3-7}$cycloalkyl or a radical of formula —Alk—$R^7$ (c-1)

or

—Alk—Z—$R^8$ (c-2);

wherein Alk is $C_{1-6}$alkanediyl;
Z is a bivalent radical of formula —O—, —S— or —N$R^3$—;
$R^7$ is phenyl; phenyl substituted with 1 or 2 substituents selected from halo, $C_{1-6}$alkyl and $C_{1-6}$alkyloxy; furanyl; furanyl substituted with 1 or 2 substituents selected from $C_{1-6}$alkyl and hydroxy$C_{1-6}$alkyl; thienyl; thienyl substituted with 1 or 2 substituents selected from halo and $C_{1-6}$alkyl;
oxazolyl; oxazolyl substituted with 1 or 2 $C_{1-6}$alkyl substituents;
thiazolyl; thiazolyl substitued with 1 or 2 $C_{1-6}$alkyl substituents;
$R^8$ is $C_{1-6}$alkyl or $C_{1-6}$alkyl substituted with hydroxy, carboxyl or $C_{1-6}$alkyloxycarbonyl;
$R^5$ is hydrogen, halo, hydroxy or $C_{1-6}$alkyloxy;
$R^6$ is hydrogen, $C_{1-6}$alkyl or $Ar^1C_{1-6}$alkyl;
$Ar^1$ is phenyl; phenyl substituted with 1, 2 or 3 substituents each independently selected from halo, $C_{1-4}$alkyl, halo$C_{1-4}$alkyl, cyano, aminocarbonyl, $C_{1-4}$alkyloxy and halo$C_{1-4}$alkyloxy;
$Ar^2$ is naphtalenyl; phenyl; phenyl substituted with 1, 2 or 3 substituents each independently selected from hydroxy, halo, cyano, nitro, amino, mono- or di($C_{1-4}$alkyl)amino, $C_{1-4}$alkyl, halo$C_{1-4}$alkyl, $C_{1-4}$alkyloxy, halo$C_{1-4}$alkyloxy, carboxyl, $C_{1-4}$alkyloxycarbonyl, aminocarbonyl and mono- or di($C_{1-4}$alkyl)aminocarbonyl; and
Het is a monocyclic heterocycle selected from pyrrolyl, pyrazolyl, imidazolyl, furanyl, thienyl, oxazolyl, isoxazolyl, thiazolyl and isothiazolyl; or a bicyclic heterocycle selected from indolyl, benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl and mono-, di- or tri(halo)methyl.

2. A compound according to claim 1 wherein L is a radical of formula (B) and Het is a monocyclic heterocycle selected from pyrrolyl, pyrazolyl, imidazolyl, furanyl, thienyl, oxazolyl, isoxazolyl, thiazolyl and isothiazolyl; or a bicyclic heterocycle selected from benzimidazolyl, benzoxazolyl, benzisoxazolyl, benzothiazolyl, benzisothiazolyl, benzofuranyl and benzothienyl; each monocyclic and bicyclic heterocycle may optionally be substituted on a carbon atom by 1 or 2 substituents selected from halo, $C_{1-4}$alkyl and mono-, di- or tri(halo)methyl.

3. A compound according claim 1 wherein L is a radical of formula (B), n is 1 or 2, and m is 1 or 2, provided that if m is 2, then n is 1.

4. A compound according claim 1 wherein $R^1$ is $Ar^1C_{1-6}$alkyl, $R^2$ is phenyl substituted with 2 substituents selected from methyl and trifluoromethyl, X is a covalent bond and =Q is =O.

5. A compound according claim 1 wherein ⁔Y— is —NH— or —O—; —A=B— is —CH=CH— or —N=CH—; $R^4$ is a radical of formula (c-1) wherein $R^7$ is oxazolyl substituted with 1 or 2 $C_{1-6}$alkyl substituents, furanyl substituted with $C_{1-6}$alkyl or hydroxy$C_{1-6}$alkyl; or $R^4$ is a radical of formula (c-2) wherein Z is a bivalent radical of formula —O—, and $R^8$ is $C_{1-6}$alkyl; $R^5$ is hydrogen; and $R^6$ is hydrogen.

6. A compound according to claim 1 selected from
1-[3,5-bis(trifluoromethyl)benzoyl]-4-[[1-(2-ethoxyethyl)-1H-benzimidazol-2-yl]amino]-2-(phenylmethyl)piperidine;
1-[3,5-bis(trifluoromethyl)benzoyl]-4-[[1-[(2-methyl-4-oxazolyl)methyl]-1H-benzimidazol-2-yl]amino]-2-(phenylmethyl)piperidine;
1-[3,5-bis(trifluoromethy benzoyl]-4-[[1-[(5-methyl-2-furanyl)methyl]-1H-benzimidazol-2-yl]amino]-2-(phenylmethyl)piperidine; a stereoisomeric form or a pharmaceutically acceptable acid addition salt thereof.

7. A pharmaceutical composition comprising a pharmaceutically acceptable carrier, and as active ingredient a therapeutically effective amount of a compound as claimed in claim 1.

8. A method for treating a warm-blooded animal suffering from a tachykinin-mediated disease comprising administering to the animal a therapeutically effective amount of a compound as claimed in claim 1.

9. The method of claim 8, wherein the tachykinin-mediated disease is selected from asthma, pain and emesis.

10. A method for treating a warm-blooded animal suffering from asthma comprising administering to the animal a therapeutically effective amount of a compound as claimed in claim 1.

11. A process of preparing a compound as claimed in claim 1, characterized by
a) reacting an intermediate of formula (II) wherein $R^2$, X and Q are defined as in claim 1 and $W^1$ is an appropriate leaving group, with an intermediate of formula (III)

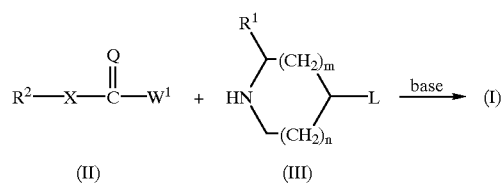

wherein n, m, L and $R^1$ are defined as in claim 1, in a reaction-inert solvent, and in 20 the presence of a suitable base;

b) reductively N-alkylating an intermediate of formula (VI) wherein —A=B—, $R^3$, $R^4$ and $R^5$ are defined as in claim 1, with an intermediate of formula (IV)

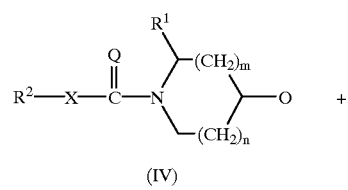

-continued

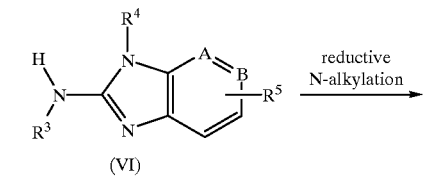

(VI)

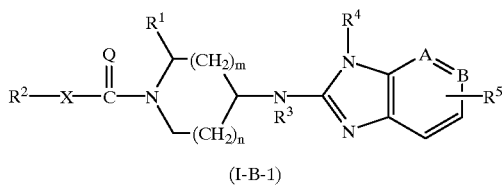

(I-B-1)

wherein $R^1$, $R^2$, X, Q, n and m are defined as in claim 1, in a reaction-inert solvent, in the presence of a reducing agent and optionally in the presence of a suitable catalyst; thus forming a compound of formula (I-B-1);

c) reacting an intermediate of formula (VII) wherein $R^1$, $R^2$, $R^3$, X, Q, n and m are defined as in claim 1, with an intermediate of formula (VIII)

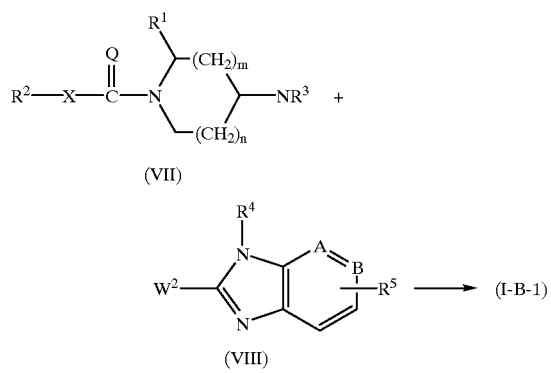

wherein $W^2$ is an appropriate leaving group and —A=B—, $R^4$ and $R^5$ are defined as in claim 1, in the presence of a suitable catalyst and optionally in a reaction-inert solvent; thus forming a compound of formula (I-B-1);

d) reacting an intermediate of formula (IX) wherein $W^3$ is a suitable leaving group and $R^1$, $R^2$, X, Q, n and m are defined as in claim 1, with an intermediate of formula (X)

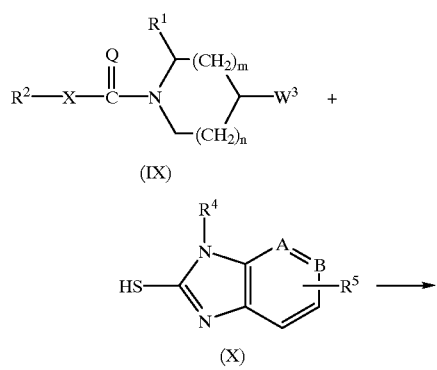

-continued

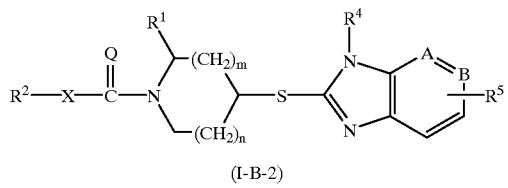

(I-B-2)

wherein —A=B—, $R^4$ and $R^5$ are defined as in claim 1, in a reaction-inert solvent, and in the presence of a suitable base; thus forming a compound of formula (I-B-2); or e) reacting an intermediate of formula (XI) wherein $R^1$, $R^2$, X, Q, n and m are defined as in claim 1, with an intermediate of formula (VIII)

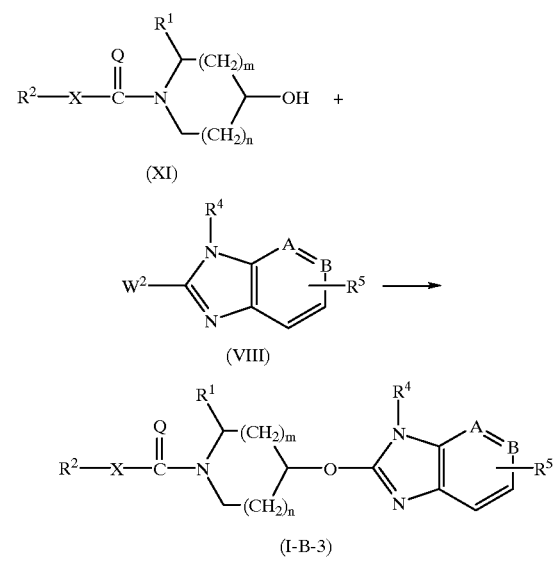

(I-B-3)

wherein $W^2$ is an appropriate leaving group and —A=B—, $R^4$ and $R^5$ are defined as in claim 1, in a reaction-inert solvent and in the presence of a suitable base; thus forming a compound of formula (I-B-3);

and if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms or N-oxide forms thereof.

12. The method of claim 11, wherein the central nervous system disorder is selected from schizoprenia, mania, dementia, Alzheimer's disease, anxiety, AIDS-related dementia, diabetic neuropathy, multiple sclerosis, depression, Parkinson's disease, drug dependence and substance abuse.

13. The method of claim 12, wherein the disorder is selected from depression and anxiety.

14. A method of treating a central nervous system disorder comprising administering to a warm-blooded animal a therapeutically effective amount of the compound of claim 1.

15. A process of preparing a composition as claimed in claim 7 comprising intimately mixing a pharmaceutically acceptable carrier with a therapeutically effective amount of the compound.

* * * * *